US012698245B2

(12) United States Patent
Lotz et al.

(10) Patent No.: US 12,698,245 B2
(45) Date of Patent: Aug. 4, 2026

(54) PROCESSES FOR PRODUCING POLY ALPHA OLEFINS AND METHOD OF ANALYSIS AND APPARATUSES THEREFOR

(71) Applicant: ExxonMobil Chemical Patents Inc., Baytown, TX (US)

(72) Inventors: Monica D. Lotz, Houston, TX (US); Frank N. Raushel, Baytown, TX (US); Timothy M. Boller, Houston, TX (US); Mark H. Li, Sugar Land, TX (US); Kyle G. Lewis, Houston, TX (US); Jennifer L. Rapp, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 394 days.

(21) Appl. No.: 17/633,913

(22) PCT Filed: Jun. 3, 2020

(86) PCT No.: PCT/US2020/035809
§ 371 (c)(1),
(2) Date: Feb. 8, 2022

(87) PCT Pub. No.: WO2021/029938
PCT Pub. Date: Feb. 18, 2021

(65) Prior Publication Data

US 2022/0298087 A1 Sep. 22, 2022

Related U.S. Application Data

(60) Provisional application No. 62/884,991, filed on Aug. 9, 2019.

(30) Foreign Application Priority Data

Oct. 24, 2019 (EP) .................................... 19205038

(51) Int. Cl.
*C07C 2/34* (2006.01)
*C07C 5/25* (2006.01)
*C10M 177/00* (2006.01)

(52) U.S. Cl.
CPC .................. *C07C 2/34* (2013.01); *C07C 5/25* (2013.01); *C10M 177/00* (2013.01);
(Continued)

(58) Field of Classification Search
None
See application file for complete search history.

(56) References Cited

U.S. PATENT DOCUMENTS

| | | | |
|---|---|---|---|
| 3,852,207 | A | 12/1974 | Stangeland et al. |
| 3,904,513 | A | 9/1975 | Fischer et al. |

(Continued)

FOREIGN PATENT DOCUMENTS

| | | | |
|---|---|---|---|
| EP | 0426638 | A2 | 8/1991 |
| WO | 97/22635 | A1 | 6/1997 |

(Continued)

OTHER PUBLICATIONS

Patience, Gregory S . . . (2018). "Experimental Methods and Instrumentation for Chemical Engineers (2nd Edition)—9.3. Gas Chromatography" pp. 263 and 273 Elsevier. Retrieved from <br>https://app.knovel.com/hotlink/pdf/id:kt00CXGDG1/experimental-methods/columns (Year: 2018).*

(Continued)

*Primary Examiner* — In Suk C Bullock
*Assistant Examiner* — Alyssa L Cepluch
(74) *Attorney, Agent, or Firm* — Vorys, Sater, Seymour and Pease LLP

(57) ABSTRACT

The present disclosure provides processes and apparatus for producing poly alpha olefins. In at least one embodiment, a process to produce a poly alpha olefin includes introducing
(Continued)

a first olefin monomer to a first catalyst and an activator in a first reactor to form a first reactor effluent comprising an olefin dimer and an olefin trimer. The process includes introducing the first reactor effluent to a filtration unit to form a filtration effluent, and introducing the filtration effluent to a first distillation unit to form a first distillation effluent. The process includes introducing the first distillation effluent (or a second distillation effluent) to a second catalyst in a second reactor to form a second reactor effluent comprising the olefin trimer. The process includes removing a sample at any stage of the process and introducing the sample to a gas chromatograph.

21 Claims, 7 Drawing Sheets

(52) U.S. Cl.
CPC ...... *C07C 2531/14* (2013.01); *C07C 2531/22* (2013.01); *C10M 2205/0285* (2013.01)

(56) References Cited

U.S. PATENT DOCUMENTS

| | | | | |
|---|---|---|---|---|
| 4,125,569 | A | 11/1978 | Jackson | |
| 4,157,294 | A | 6/1979 | Iwao et al. | |
| 4,568,786 | A * | 2/1986 | Hsia Chen | C10G 50/02 585/533 |
| 4,673,487 | A | 6/1987 | Miller | |
| 5,241,025 | A | 8/1993 | Hlatky et al. | |
| 5,284,988 | A * | 2/1994 | Schaerl, Jr. | C10G 50/02 585/16 |
| 5,447,895 | A | 9/1995 | Marks et al. | |
| 6,548,724 | B2 | 4/2003 | Bagheri et al. | |
| 7,511,104 | B2 | 3/2009 | Pehlert et al. | |
| 9,365,788 | B2 | 6/2016 | Emett et al. | |
| 2007/0043248 | A1 | 2/2007 | Wu et al. | |
| 2009/0156874 | A1 | 6/2009 | Patil et al. | |
| 2009/0240012 | A1 * | 9/2009 | Patil | C07C 2/34 526/348 |
| 2010/0292420 | A1 | 11/2010 | Fushimi et al. | |
| 2010/0292424 | A1 | 11/2010 | Wu et al. | |
| 2011/0135904 | A1 * | 6/2011 | Iwase | C08J 9/0033 428/220 |
| 2011/0251445 | A1 * | 10/2011 | Takeuchi | C07C 2/34 585/16 |
| 2013/0090277 | A1 | 4/2013 | Martin et al. | |
| 2014/0275664 | A1 * | 9/2014 | Yang | C10M 107/10 585/18 |
| 2018/0037521 | A1 * | 2/2018 | Islam | C07C 2/34 |

FOREIGN PATENT DOCUMENTS

| | | | |
|---|---|---|---|
| WO | 2006/108698 | A1 | 10/2006 |
| WO | 2007/011973 | A1 | 1/2007 |
| WO | 2010/002485 | A1 | 1/2010 |
| WO | 2010/147993 | A1 | 12/2010 |
| WO | 2012/134688 | A1 | 10/2012 |
| WO | 2013/130952 | A1 | 9/2013 |
| WO | 2021/029938 | A1 | 2/2021 |

OTHER PUBLICATIONS

LCGC "The Chromatography and Sample Preparation Guide" Volumn 31, S10, pp. 1-82 (Year: 2013).*

Hergeth "On-Line Monitoring of Chemical Reactions" Ullmann's Encyclopedia of Industrial Chemistry. Chapters 7 and 9, pp. 345-397 (Year: 2012).*

Lovestead "Gas Chromatography" ATSM Handbook, vol. 10, Materials Characterization. pp. 229-234 (Year: 2019).*

Extended European Search Report received for European Patent Application No. 19205038.3 mailed on Aug. 17, 2020, 8 Pages.

International Preliminary Report on Patentability received for PCT Application No. PCT/US2020/035809, mailed on Feb. 17, 2022, 12 Pages.

International Search Report and Written Opinion received for PCT Application No. PCT/US2020/035809, mailed on Dec. 2, 2020, 16 Pages.

* cited by examiner

PROCESSES FOR PRODUCING POLY ALPHA OLEFINS AND METHOD OF ANALYSIS AND APPARATUSES THEREFOR

CROSS-REFERENCE TO RELATED APPLICATION

This application is a National Phase Application claiming priority to PCT Application Serial No. PCT/US2020/035809 filed Jun. 3, 2020, which claims the benefit of U.S. Provisional Application No. 62/884,991 filed Aug. 9, 2019 entitled "Processes for Producing Poly Alpha Olefins and Method Of Analysis And Apparatuses Therefor", the entirety of which is incorporated by reference herein.

This application is related to U.S. Ser. No. 62/885,014, (2019EM299) entitled "Processes for Producing Poly Alpha Olefins and Apparatuses Thereof," filed Aug. 9, 2019.

FIELD

The present disclosure provides processes and apparatuses for producing poly alpha olefins.

BACKGROUND

Efforts to improve the performance of lubricant basestocks by the oligomerization of hydrocarbon fluids have been ongoing in the petroleum industry for over fifty years. These efforts have led to the market introduction of a number of synthetic lubricant basestocks. Much of the research involving synthetic lubricant basestocks has been toward developing fluids that exhibit useful viscosities over a wide temperature range while also maintaining lubricities, thermal and oxidative stabilities, and pour points equal to or better than those for mineral lubricants.

The viscosity-temperature relationship of a lubricant is one criterion that can be considered when selecting a lubricant for a particular application. The viscosity index (VI) is an empirical number which indicates the rate of change in the viscosity of an oil within a given temperature range. A high VI oil will thin out at elevated temperatures slower than a low VI oil. In most lubricant applications, a high VI oil is desirable because maintaining a higher viscosity at higher temperatures translates into better lubrication.

Poly alpha olefins (PAOs) are a class of materials that are exceptionally useful as high performance synthetic lubricant basestocks. PAOs possess excellent flow properties at low temperatures, good thermal and oxidative stability, low evaporation losses at high temperatures, high viscosity index, good friction behavior, good hydrolytic stability, and good erosion resistance. PAOs are miscible with mineral oils, other synthetic hydrocarbon liquids, fluids and esters. Consequently, PAOs are suitable for use in engine oils, compressor oils, hydraulic oils, gear oils, greases, and functional fluids.

Although most of the research on metallocene-based PAOs has focused on higher viscosity oils, recent research has looked at producing low viscosity PAOs for automotive applications. A current trend in the automotive industry is toward extending oil drain intervals and improving fuel economy. This trend is driving increasingly stringent performance requirements for lubricants. New PAOs with improved properties such as high viscosity index, low pour point, high shear stability, improved wear performance, increased thermal and oxidative stability, and/or wider viscosity ranges are needed to meet these new performance requirements. New processes to produce such PAOs are also needed.

US 2007/043248 discloses a process using a metallocene catalyst for the production of low viscosity (4 to 10 cSt) PAO basestocks. This technology is attractive because the metallocene-based low viscosity PAO has excellent lubricant properties. One disadvantage of the low viscosity metallocene-catalyzed process is that a significant amount of dimer is formed. This dimer is typically not useful as a lubricant basestock because it has very poor low temperature and volatility properties. Recent industry research has looked at recycling the dimer portion formed in the metallocene-catalyzed process into a subsequent oligomerization process. However, recycling the dimer portion into a subsequent oligomerization process is selective for only certain dimeric structures of the recycled feed. In fact, in some industrial processes, higher amounts of one isomer starting material (cis- or trans-) versus the other isomer can provide higher overall yields of final products. However, there is currently no reliable process of analyzing various dimeric structures and trimeric structures in real-time (e.g., a process that can be performed quickly enough for commercial scale poly alpha olefin production). For example, carbon nuclear magnetic resonance ($C^{13}$ NMR) can be used to discern dimeric from trimeric structures, but cannot discern cis-trisubstituted dimers from trans-trisubstituted dimers. Additionally, $C^{13}$ NMR cannot analyze various dimeric structures and trimeric structures in a commercial scale poly alpha olefin production due to the large amount of time needed to acquire a $C^{13}$ NMR spectrum (due to the large number of transients involved to obtain a $C^{13}$ NMR spectrum due to low natural abundance of carbon-13 atoms (i.e., 1% natural abundance of $C^{13}$). An NMR spectrometer can only detect $C^{13}$ atoms (and cannot detect the much more naturally abundant carbon-12 atoms ($C^{12}$ atoms)). Furthermore, although much faster than $C^{13}$ NMR, hydrogen nuclear magnetic resonance ($H^1$ NMR) cannot be used to discern (1) dimeric from trimeric structures or (2) cis-trisubstituted dimers from trans-trisubstituted dimers.

There is a need for improved processes and apparatuses for monitoring dimer production in commercial scale poly alpha olefin production, such as production of low viscosity poly alpha olefins.

References for citing in an Information Disclosure Statement (37 CFR 1.97(h): U.S. Pat. Nos. 9,365,788; 6,548,724; 5,284,988; U.S. Patent Publication Nos. 2013/090277; 2007/043248; 2013/130952; PCT Publication No. WO 2012/134688.

SUMMARY

In at least one embodiment, a process to produce a poly alpha olefin includes introducing an olefin monomer to a catalyst and an activator in a reactor to form a reactor effluent comprising an olefin dimer and an olefin trimer. The method includes introducing the reactor effluent to a filtration unit to form a filtration effluent. The method includes introducing the filtration effluent to a first distillation unit to form a first distillation effluent. The method may include optionally introducing the first distillation effluent to an optional second distillation unit to form a second distillation effluent. The method includes removing a sample from (1) the reactor, (2) a line coupling the reactor to the filtration unit, (3) a line coupling the filtration unit to the distillation unit, or (4) a line coupling the first distillation unit to the optional second distillation unit. The method includes introducing the sample to a gas chromatograph.

In at least one embodiment, a process to produce a poly alpha olefin include introducing a first olefin monomer to a first catalyst and an activator in a first reactor to form a first reactor effluent comprising an olefin dimer and an olefin trimer. The process includes introducing the first reactor effluent to a first distillation unit to form a first distillation effluent, and introducing the first distillation effluent to a second distillation unit to form a second distillation effluent. The process includes introducing the second distillation effluent to a second catalyst in a second reactor to form a second reactor effluent comprising the olefin trimer. The process includes removing a sample from (1) the first reactor (2) a line coupling the first reactor to the first distillation unit; (3) a line coupling the first distillation unit to the second distillation unit, or (4) a line coupling the distillation unit to the second reactor. The process includes introducing the sample to a gas chromatograph having a column coated with a material.

In at least one embodiment, a process to produce a poly alpha olefin includes introducing a first olefin monomer to a first catalyst and an activator in a first reactor to form a first reactor effluent comprising an olefin dimer and an olefin trimer. The process includes introducing the first reactor effluent to a first distillation unit to form a first distillation effluent, and introducing the first distillation effluent to a second distillation unit to form a second distillation effluent. The process includes introducing the second distillation effluent to a second catalyst in a second reactor to form a second reactor effluent comprising the olefin trimer. The process includes removing a sample from (1) the first reactor, (2) a line coupling the first reactor to the first distillation unit; (3) a line coupling the first distillation unit to the second distillation unit, or (4) a line coupling the distillation unit to the second reactor. The process includes introducing the sample to a gas chromatograph.

In at least one embodiment, an apparatus includes a first reactor coupled at a first end with a first end of a first distillation unit via a first line. The reactor includes a gas chromatograph coupled at a first end with the first line. The reactor includes a second distillation unit coupled with (1) a second end of the first distillation unit at a first end of the second distillation unit, (2) a first end of a second reactor at a second end of the second distillation unit via a second line, and (3) a first end of a hydrogenation unit at a third end of the second distillation unit.

In at least one embodiment, an apparatus includes a first reactor coupled at a first end with a first end of a filtration unit. The apparatus includes a first distillation unit coupled at a first end with a second end of the filtration unit. The apparatus includes a second distillation unit coupled with (1) a second end of the first distillation unit, via a first line, at a first end of the second distillation unit, (2) a first end of a second reactor, via a second line, at a second end of the second distillation unit, and (3) a first end of a hydrogenation unit at a third end of the second distillation unit. The apparatus includes a gas chromatograph coupled at a first end with the second line.

BRIEF DESCRIPTION OF THE DRAWINGS

So that the manner in which the above recited features of the present disclosure can be understood in detail, a more particular description of the disclosure, briefly summarized above, may be had by reference to examples, some of which are illustrated in the appended drawings. It is to be noted, however, that the appended drawings illustrate only typical examples of this present disclosure and are therefore not to be considered limiting of its scope, for the present disclosure may admit to other equally effective examples.

To facilitate understanding, identical reference numerals have been used, where possible, to designate identical elements that are common to the figures. It is contemplated that elements and features of one example may be beneficially incorporated in other examples without further recitation.

DETAILED DESCRIPTION

Figure 1:
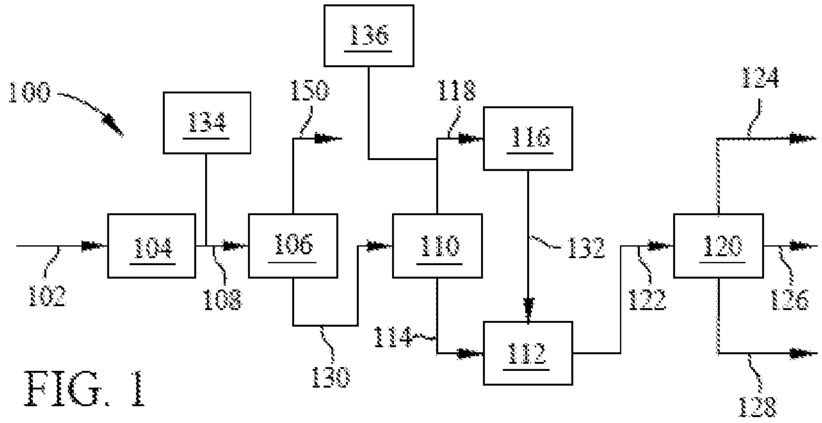
FIG. 1 is an apparatus for forming poly alpha olefins, according to at least one embodiment.

The present disclosure provides processes and apparatuses for producing poly alpha olefins. In at least one embodiment, a process includes oligomerizing linear alpha olefins to form vinylidene dimers. The process includes measuring by gas chromatography an amount of one or more of vinylidene dimers and/or trisubstituted dimers (such as cis-trisubstituted dimers and trans-trisubstituted dimers). The process includes optionally isomerizing the vinylidene dimers to form tri-substituted olefin dimers (such as cis-trisubstituted dimers and trans-trisubstituted dimers), and oligomerizing the tri-substituted olefin dimers to form trimers. Tri-substituted olefin dimers provide higher selectivity (than vinylidene dimers) to trimers in an oligomerization process. Isomerization of vinylidene dimers to tri-substituted olefin dimers provides higher overall yields of trimers. The process can further include hydrogenating the trimers to form saturated trimers.

It has further been discovered that vinylidene dimers can be isomerized in the absence of added isomerization catalyst, rendering isomerization in an additional reactor merely optional. A heat exchanger can be coupled with a line transporting the vinylidene dimers from a first reactor (such as a reactor configured to oligomerize linear alpha olefins to form vinylidene dimers) to a filtration unit and/or to a distillation unit. Additionally or alternatively, a heat exchanger can be coupled with a line transporting vinylidene dimers from a distillation unit to a second reactor (such as a reactor configured to oligomerize tri-substituted olefin dimers to form trimers). In some embodiments, an amount of one or more of vinylidene dimers and/or trisubstituted dimers can be measured during an trimer production process by (1) a gas chromatograph coupled with the line transporting the vinylidene dimers from the first reactor to the filtration unit and/or the distillation unit, and/or (2) the gas chromatograph (or a different gas chromatograph) coupled with the line transporting vinylidene dimer from the distillation unit to the second reactor.

Isomerizing vinylidene dimers in the absence of an added isomerization catalyst (and/or in the absence of an isomerization reactor) provides substantial cost savings and throughput enhancement as compared to conventional poly alpha olefin processes. Furthermore, isomerizing vinylidene dimers in the absence of an added isomerization catalyst renders merely optional a filtration unit coupled with the first reactor. However, filtration is typically used to filter particulates. Additionally or alternatively, a less expensive and less complex filtration unit can be used (such as a crude particulate filter having a large pore size) instead of a conventional cellulosic body feed-type filtration unit, which provides additional cost savings and throughput enhancement.

In addition, measuring by gas chromatography an amount of one or more of vinylidene dimers and/or trisubstituted dimers (such as cis-trisubstituted dimers and/or trans-trisubstituted dimers) can provide monitoring of dimer formation in commercial scale poly alpha olefin production, such as production of low viscosity poly alpha olefins. For example, the measuring may be used to determine whether (1) reactor conditions in the first reactor should be adjusted to promote dimer formation, (2) distillation conditions (e.g., cut point) of a distillation unit should be adjusted, and/or (3) heating should be provided to a line transferring effluent from the first reactor and/or transferring effluent from a distillation unit to the second reactor.

When used in the present disclosure, in accordance with conventional terminology in the art, the following terms are defined for the sake of clarity. The term "vinyl" is used to designate groups of formula $RCH{=}CH_2$. The term "vinylidene" is used to designate groups of formula $RR'{=}CH_2$. The term "disubstituted vinylene" is used to designate groups of formula $RCH{=}CHR'$. The term "trisubstituted vinylene" is used to designate groups of formula $RR'C{=}CHR''$. The term "tetrasubstituted vinylene" is used to designate groups of formula $RR'C{=}CR''R'''$. For all of these formulas, R, R', R'', and R''' are alkyl groups which may be identical or different from each other.

The monomer feed used in both (1) the first oligomerization and optionally contacted with the recycled intermediate PAO dimer and (2) light olefin fractions in the subsequent oligomerization is at least one linear alpha olefin (LAO). The LAO may be comprised of monomers of 6 to 24 carbon atoms, usually 6 to 20, such as 6 to 14 carbon atoms, such as 1-hexene, 1-octene, 1-nonene, 1-decene, 1-dodecene, and 1-tetradecene. Olefins with even carbon numbers can be the LAO used. Additionally, the olefins can be treated to remove catalyst poisons, such as peroxides, oxygen, sulfur, nitrogen-containing organic compounds, and/or acetylenic compounds as described in WO 2007/011973.

For the purposes of the present disclosure, the numbering scheme for the Periodic Table Groups is used as described in *Chemical and Engineering News*, v.63(5), pg. 27 (1985). Therefore, a "Group 8 metal" is an element from Group 8 of the Periodic Table, e.g., Fe.

First Oligomerization

Catalyst

Useful catalysts in the first oligomerization (e.g., in a first reactor) include single site catalysts. For example, the first oligomerization can utilize a metallocene catalyst. In this disclosure, the terms "metallocene catalyst" and "transition metal compound" are used interchangeably. Catalysts can give high catalyst productivity and result in a product having low viscosity and low molecular weight. Metallocene catalysts may be bridged or unbridged and substituted or unsubstituted. They may have leaving groups including dihalides or dialkyls. When the leaving groups are dihalides, trialkylaluminum may be used to promote the reaction. In general, useful transition metal compounds may be represented by the following formula:

$$X^1X^2M^1(cpcp^*)M^2X^3X^4$$

wherein:

$M^1$ is an optional bridging element, such as selected from silicon or carbon;

$M^2$ is a Group 4 metal;

each of Cp and Cp * are the same or different substituted or unsubstituted cyclopentadienyl ligand systems wherein, if substituted, the substitutions may be independent or linked to form multicyclic structures;

each of $X^1$ and $X^2$ is independently hydrogen, hydride radicals, hydrocarbyl radicals, substituted hydrocarbyl radicals, silylcarbyl radicals, substituted silylcarbyl radicals, germylcarbyl radicals, or substituted germylcarbyl radicals or are independently selected from hydrogen, branched or unbranched $C_1$ to $C_{20}$ hydrocarbyl radicals, or branched or unbranched substituted $C_1$ to $C_{20}$ hydrocarbyl radicals; and each of $X^3$ and $X^4$ is independently hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, substituted germylcarbyl radicals, or $X^3$ and $X^4$ are joined and bound to the metal atom to form a metallacycle ring containing from about 3 to about 20 carbon atoms, or are independently selected from hydrogen, branched or unbranched $C_1$ to $C_{20}$ hydrocarbyl radicals, or branched or unbranched substituted $C_1$ to $C_{20}$ hydrocarbyl radicals.

For this disclosure, a hydrocarbyl radical is a $C_1$-$C_{100}$ radical and may be linear, branched, or cyclic. In at least one embodiment, a substituted hydrocarbyl radical includes halocarbyl radicals, substituted halocarbyl radicals, silylcarbyl radicals, and germylcarbyl radicals.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, $—Si(R^*)_2—$, $—Ge(R^*)_2—$, $—Sn(R^*)_2—$, $—Pb(R^*)_2—$, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g., $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SPR^*_2$, $SR^*$, $BR^*_2$, $SiR^*_3$, $GeR^*_3$, $SnR^*_3$, $PbR^*_3$, or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, $—Si(R^*)_2—$, $—Ge(R^*)_2—$, $—Sn(R^*)_2—$, $—Pb(R^*)_2—$, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^*_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, where R* is independently a hydrocarbyl or halocarbyl radical and two or more R* may join together to form a substituted or unsubstituted saturated, partially unsaturated or aromatic cyclic or polycyclic ring structure.

In at least one embodiment, the transition metal compound may be represented by the following formula:

$$X^1X^2M^1(CpCp^*)M^2X^3X^4$$

wherein:

- $M^1$ is a bridging element, such as silicon;
- $M^2$ is a Group 4 metal, such as titanium, zirconium or hafnium;
- Cp and Cp * are the same or different substituted or unsubstituted indenyl or tetrahydroindenyl rings that are each bonded to both $M^1$ and $M^2$;
- $X^1$ and $X^2$ are independently hydrogen, hydride radicals, hydrocarbyl radicals, substituted hydrocarbyl radicals, silylcarbyl radicals, substituted silylcarbyl radicals, germylcarbyl radicals, or substituted germylcarbyl radicals; and
- $X^3$ and $X^4$ are independently hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both $X^3$ and $X^4$ are joined and bound to the metal atom to form a metallacycle ring containing from about 3 to about 20 carbon atoms.

In using the terms "substituted or unsubstituted tetrahydroindenyl," "substituted or unsubstituted tetrahydroindenyl ligand," the substitution to the aforementioned ligand may be hydrocarbyl, substituted hydrocarbyl, halocarbyl, substituted halocarbyl, silylcarbyl, or germylcarbyl. The substitution may also be within the ring giving heteroindenyl ligands or heterotetrahydroindenyl ligands, either of which can additionally be substituted or unsubstituted.

In another embodiment, useful transition metal compounds may be represented by the following formula:

$$L^AL^BL^C_iMDE$$

wherein:

- $L^A$ is a substituted cyclopentadienyl or heterocyclopentadienyl ancillary ligand π-bonded to M;
- $L^B$ is a member of the class of ancillary ligands recited for $L^A$, or is J, wherein J is a heteroatom ancillary ligand σ-bonded to M; the $L^A$ and $L^B$ ligands may be covalently bridged together through a Group 14 element linking group;
- $L^C_i$ is an optional neutral, non-oxidizing ligand having a dative bond to M (i equals 0 to 3);
- M is a Group 4 or 5 transition metal; and
- D and E are independently monoanionic labile ligands, each having a η-bond to M, optionally bridged to each other or $L^A$ or $L^B$. The mono-anionic ligands are displaceable by a suitable activator to permit insertion of a polymerizable monomer or a macro-monomer can insert for coordination polymerization on the vacant coordination site of the transition metal compound.

In at least one embodiment, an oligomerization process utilizes a highly active metallocene catalyst. For example, the catalyst productivity may be greater than about 15,000 g PAO/g catalyst, such as greater than about 20,000 g PAO g catalyst, such as greater than about 25,000 g PAO/g catalyst, such as greater than about 30,000 g PAO g catalyst, wherein g PAO/g catalyst represents grams of PAO formed per grams of catalyst used in the oligomerization reaction.

High productivity rates are also achieved. In at least one embodiment, the productivity rate in the first oligomerization is greater than about 4,000 g PAO/g catalyst*hour (also referred to as "gPAO/g catalyst/h"), such as greater than about 6,000 g PAO/g catalyst*hour, such as greater than about 8,000 g PAO/g catalyst * hour, such as greater than about 10,000 g PAO g catalyst*hour, wherein g PAO/g catalyst represents grams of PAO formed per grams of catalyst used in the oligomerization reaction.

Activator

The catalyst may be activated by any suitable activator such as a non-coordinating anion (NCA) activator. An NCA is an anion which either does not coordinate to the catalyst metal cation or that coordinates only weakly to the metal cation. An NCA coordinates weakly enough that a neutral Lewis base, such as an olefinically or acetylenically unsaturated monomer, can displace it from the catalyst center. Any metal or metalloid that can form a compatible, weakly coordinating complex with the catalyst metal cation may be used or contained in the NCA. Suitable metals include aluminum, gold, and platinum. Suitable metalloids include boron, aluminum, phosphorus, and silicon.

Lewis acid and ionic activators may also be used. Useful but non-limiting examples of Lewis acid activators include triphenylboron, tris-perfluorophenylboron, and tris-perfluorophenylaluminum. Useful but non-limiting examples of ionic activators include dimethylanilinium tetrakisperfluorophenylborate, triphenylcarbenium tetrakisperfluorophenylborate, and dimethylanilinium tetrakisperfluorophenylaluminate.

An additional subclass of useful NCAs comprises stoichiometric activators, which can be either neutral or ionic. Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy, and halides. For example, the three groups can be independently selected from halogen, mono or multicyclic (including halosubstituted) aryls, alkyls, and alkenyl compounds and mixtures thereof, for example alkenyl groups having 1 to 20 carbon atoms, alkyl groups having 1 to 20 carbon atoms, alkoxy groups having 1 to 20 carbon atoms, and aryl groups having 3 to 20 carbon atoms (including substituted aryls). For example, the three groups can be alkyls having 1 to 4 carbon groups, phenyl, naphthyl, or mixtures thereof. For example, the three groups are halogenated, such as fluorinated, aryl groups. Ionic stoichiometric activator compounds may contain an active proton, or some other cation associated with, but not coordinated to, or only loosely coordinated to, the remaining ion of the ionizing compound.

Ionic catalysts can be prepared by reacting a transition metal compound with an activator, such as $B(C_6F_6)_3$, which upon reaction with the hydrolyzable ligand (X') of the transition metal compound forms an anion, such as ($[B(C_6F_5)_3(X')]^-$), which stabilizes the cationic transition metal species generated by the reaction. The catalysts can be prepared with activator components which are ionic compounds or compositions. Additionally or alternatively, activators can be prepared utilizing neutral compounds.

Compounds used as an activator component in the preparation of the ionic catalyst systems used in a process of the present disclosure can include a cation, which can be a Brønsted acid capable of donating a proton, and a compatible NCA which anion is relatively large (bulky), capable of stabilizing the active catalyst species which is formed when the two compounds are combined and said anion will be sufficiently labile to be displaced by olefinic, diolefinic, and acetylenically unsaturated substrates or other neutral Lewis bases such as ethers or nitriles.

In at least one embodiment, the ionic stoichiometric activators include a cation and an anion component, and may be represented by the following formula:

$$(L^{**}-H)_d^+(A_d^-)$$

wherein:

L** is an neutral Lewis base;

H is hydrogen;

$(L^{**}-H)^+$ is a Brønsted acid or a reducible Lewis acid; and $A_d^-$ is an NCA having the charge d-, and d is an integer from 1 to 3.

The cation component, $(L^{**}-H)_d^+$ may include Brønsted acids such as protons or protonated Lewis bases or reducible Lewis acids capable of protonating or abstracting a moiety, such as an alkyl or aryl, from the catalyst after alkylation.

The activating cation $(L^{}-H)_d^+$ may be a Brønsted acid, capable of donating a proton to the alkylated transition metal catalytic precursor resulting in a transition metal cation, including ammoniums, oxoniums, phosphoniums, silyliums, and mixtures thereof, such as ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation $(L^{}-H)_d^+$ may also be a moiety such as silver, tropylium, carbeniums, ferroceniums and mixtures, such as carbeniums and ferroceniums; such as triphenyl carbenium. The anion component $A_d^-$ includes those having the formula $[Mk+Qn]_d^-$ wherein k is an integer from 1 to 3; n is an integer from 2-6; n−k=d; M is an element selected from Group 13 of the Periodic Table of the Elements, such as boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. For example, each Q is a fluorinated hydrocarbyl group having 1 to 20 carbon atoms, such as each Q is a fluorinated aryl group, such as each Q is a pentafluoryl aryl group. Examples of suitable $A_d^-$ also include diboron compounds as disclosed in U.S. Pat. No. 5,447,895, which is incorporated herein by reference.

Boron compounds which may be used as an NCA activator in combination with a co-activator are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis (pentafluorophenyl)borate, tri(n-butyl)ammonium tetrakis (pentafluorophenyl)borate, tri(sec-butyl)ammonium tetrakis (pentafluorophenyl)borate, N,N-dimethylanilinium tetrakis (pentafluorophenyl)borate, N,N-diethylanilinium tetrakis (pentafluorophenyl)borate, N,N-dimethyl-(2,4,6-trimethylanilinium)tetrakis(pentafluorophenyl)borate, trimethylammonium tetrakis-(2,3,4,6-tetrafluorophenyl)borate, triethylammonium tetrakis-(2,3,4,6-tetrafluorophenyl) borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl) ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis (perfluoronaphthyl)borate, tri(n-butyl)ammonium tetrakis (perfluoronaphthyl)borate, tri(tert-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(tert-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl) borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene (diazonium)tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl) borate, benzene(diazonium)tetrakis-(2,3,4,6-tetrafluorophenyl)borate, tropillium tetrakis (perfluoronaphthyl)borate, triphenylcarbenium tetrakis (perfluoronaphthyl)borate, triphenylphosphonium tetrakis (perfluoronaphthyl)borate, triethylsilylium tetrakis (perfluoronaphthyl)borate, benzene(diazonium)tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium)tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium)tetrakis(3,5-bis(trifluoromethyl)phenyl)borate.

In at least one embodiment, the NCA activator, $(L^{**}—H)_d^+(A_d^-)$, is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis (trifluoromethyl)phenyl)borate, triphenylcarbenium tetrakis (perfluoronaphthyl)borate, triphenylcarbenium tetrakis (perfluorobiphenyl)borate, triphenylcarbenium tetrakis(3,5-bis(trifluoromethyl)phenyl)borate, or triphenylcarbenium tetra(perfluorophenyl)borate.

Pehlert et al., U.S. Pat. No. 7,511,104 provides additional details on NCA activators that may be useful, and these details are hereby incorporated by reference.

Additional activators that may be used include alumoxanes or alumoxanes in combination with an NCA. In one embodiment, alumoxane activators are utilized as an activator. Alumoxanes are generally oligomeric compounds containing $—Al(R^1)—O—$ sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used.

A catalyst co-activator is a compound capable of alkylating the catalyst, such that when used in combination with an activator, an active catalyst is formed. Co-activators may include alumoxanes such as methylalumoxane, modified alumoxanes such as modified methylalumoxane, and aluminum alkyls such trimethylaluminum, tri-isobutylaluminum, triethylaluminum, tri-isopropylaluminum, tri-n-hexylaluminum, tri-n-octylaluminum, tri-n-decylaluminum, and tri-n-dodecylaluminum. Co-activators are typically used in combination with Lewis acid activators and ionic activators when the catalyst is not a dihydrocarbyl or dihydride complex.

The co-activator may also be used as a scavenger to deactivate impurities in feed or reactors. A scavenger is a compound that is sufficiently Lewis acidic to coordinate with polar contaminates and impurities adventitiously occurring in the polymerization feedstocks or reaction medium. Such impurities can be inadvertently introduced with any of the reaction components, and adversely affect catalyst activity and stability. Scavenging compounds may be organometallic compounds such as triethyl aluminum, triethyl borane, tri-isobutyl aluminum, methylalumoxane, isobutyl aluminumoxane, tri-n-hexyl aluminum, tri-n-octyl aluminum, and those having bulky substituents covalently bound to the metal or metalloid center being exemplary to minimize adverse interaction with the active catalyst. Other useful scavenger compounds may include those mentioned in U.S. Pat. No. 5,241,025; EP-A 0426638; and WO 1997/022635, which are hereby incorporated by reference for such details.

The reaction time or reactor residence time can be dependent on the type of catalyst used, the amount of catalyst used, and the desired conversion level. Different transition metal compounds (also referred to as metallocene) have different activities. A high amount of catalyst loading tends to give high conversion at short reaction time. However, a high amount of catalyst usage can make the production process uneconomical and difficult to manage the reaction heat or to control the reaction temperature. Therefore, it is useful to choose a catalyst with maximum catalyst productivity to minimize the amount of metallocene and the amount of activators needed. For a catalyst system of metallocene plus a Lewis Acid or an ionic promoter with NCA component, the transition metal compound used may be from 0.01 microgram to 500 micrograms of metallocene component/gram of alpha-olefin feed, such as from 0.1 microgram to 100 microgram of metallocene component per gram of alpha-olefin feed. Furthermore, the molar ratio of the NCA activator to metallocene can be from 0.1 to 10, such as 0.5 to 5, such as 0.5 to 3. For the co-activators of alkylaluminums, the molar ratio of the co-activator to metallocene can be from 1 to 1,000, such as 2 to 500, such as 4 to 400.

In selecting oligomerization conditions, to obtain the desired first reactor effluent, the system uses the transition metal compound (also referred to as the catalyst), activator, and co-activator. US 2007/043248 and US 2010/029242 provide additional details of metallocene catalysts, activators, co-activators, and appropriate ratios of such compounds in the feedstock that may be useful, and these additional details are hereby incorporated by reference.

First Oligomerization Process Conditions

Many oligomerization processes and reactor types used for single site- or metallocene-catalyzed oligomerizations such as solution, slurry, and bulk oligomerization processes may be used for the first oligomerization. In some embodiments, if a solid catalyst is used, a slurry or continuous fixed bed or plug flow process is suitable. In at least one embodiment, the monomers can be contacted with the metallocene compound and the activator in the solution phase, bulk phase, or slurry phase, such as in a continuous stirred tank reactor or a continuous tubular reactor. In at least one embodiment, the temperature in any reactor used herein is from about −10° C. to about 250° C., such as from about 30° C. to about 220° C., such as from about 50° C. to about 180° C., such as from about 80° C. to about 150° C. In at least one embodiment, the pressure in any reactor used herein is from about 10.13 to about 10132.5 kPa (0.1 to 100 atm/1.5 to 1,500 psi), such as from about 50.66 to about 7,600 kPa (0.5 to 75 atm/8 to 1,125 psi), such as from about 101.3 to about 5,066.25 kPa (1 to 50 atm/15 to 750 psi). In another embodiment, the pressure in any reactor used herein is from about 101.3 to about 5,066,250 kPa (1 to 50,000 atm), such as about 101.3 to about 2,533,125 kPa (1 to 25,000 atm). In at least one embodiment, the residence time in any reactor is from about 1 second to about 100 hours, such as about 30 seconds to about 50 hours, such as about 2 minutes to about 6 hours, such as about 1 to about 6 hours. In another embodiment, solvent or diluent is present in the reactor. These solvents or diluents are usually pre-treated in same manners as the feed olefins.

The oligomerization can be run in batch mode, where all the components are added into a reactor and allowed to react to a degree of conversion, either partial or full conversion. Subsequently, the catalyst is deactivated by any suitable means, such as exposure to air or water, or by addition of alcohols or solvents containing deactivating agents. The oligomerization can also be carried out in a semi-continuous operation, where feeds and catalyst system components are continuously and simultaneously added to the reactor so as to maintain a constant ratio of catalyst system components to feed olefin(s). When all feeds and catalyst components are added, the reaction is allowed to proceed to a pre-determined stage. The reaction is then discontinued by catalyst deactivation in the same manner as described for batch operation. The oligomerization can also be carried out in a continuous operation, where feeds and catalyst system components are continuously and simultaneously added to the reactor so to maintain a constant ratio of catalyst system and feeds. The reaction product is continuously withdrawn from the reactor, as in a typical continuous stirred tank reactor (CSTR) operation. The residence times of the reactants are controlled by a pre-determined degree of conversion. The withdrawn product is then typically quenched in the separate reactor in a similar manner as other operation. In at least one embodiment, any of the processes to prepare PAOs described herein are continuous processes.

A production facility may have one single reactor or several reactors arranged in series or in parallel, or both, to maximize productivity, product properties, and general process efficiency. The catalyst, activator, and co-activator may be delivered as a solution or slurry in a solvent or in the LAO feed stream, either separately to the reactor, activated in-line just prior to the reactor, or pre-activated and pumped as an activated solution or slurry to the reactor. Oligomerizations are carried out in either single reactor operation, in which the monomer, or several monomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to the first reactor and another component to other reactors.

The reactors and associated equipment are usually pre-treated to ensure proper reaction rates and catalyst performance. The reaction is usually conducted under inert atmosphere, where the catalyst system and feed components will not be in contact with any catalyst deactivator or poison which is usually polar oxygen, nitrogen, sulfur or acetylenic compounds. Additionally, in one embodiment of any of the processes described herein, the feed olefins and/or solvents are treated to remove catalyst poisons, such as peroxides, oxygen or nitrogen-containing organic compounds or acetylenic compounds. Such treatment will increase catalyst productivity 2- to 10-fold or more.

The reaction time or reactor residence time is usually dependent on the type of catalyst used, the amount of catalyst used, and the desired conversion level. When the catalyst is a metallocene, different metallocenes have different activities. Usually, a higher degree of alkyl substitution on the cyclopentadienyl ring, or bridging improves catalyst productivity. High catalyst loading tends to give high conversion in short reaction time. However, high catalyst usage can make the process uneconomical and difficult to manage the reaction heat or to control the reaction temperature. Therefore, it is useful to choose a catalyst with high catalyst productivity to minimize the amount of metallocene and the amount of activators needed.

US 2007/043248 and US 2010/0292424 provide additional details on acceptable oligomerization processes using metallocene catalysts, and the details of these processes, process conditions, catalysts, activators, and co-activators are hereby incorporated by reference to the extent that they are not inconsistent with anything described in this disclosure.

Due to the low activity of some metallocene catalysts at high temperatures, low viscosity poly alpha olefins are typically oligomerized in the presence of added hydrogen at lower temperatures. An advantage is that hydrogen acts as a chain terminator, effectively decreasing molecular weight and viscosity of the poly alpha olefin. Hydrogen can also hydrogenate the olefin, however, saturating the linear alpha olefin feedstock and poly alpha olefin, which would prevent linear alpha olefin or dimers from being usefully recycled into a further oligomerization process. Thus it is an improvement to be able to make an intermediate PAO (which has dimers) without having to add hydrogen for chain termination such that the unreacted linear alpha olefin feedstock and intermediate dimers maintain their unsaturation, and thus their reactivity, for a subsequent recycle process.

The intermediate PAO produced can be a mixture of dimers (such as vinylidene dimers), trimers, and optionally tetramer and higher oligomers of the respective alpha olefin feedstocks. This intermediate PAO and portions thereof is referred to interchangeably as the "first reactor effluent" from which unreacted monomers have optionally been removed.

The intermediate PAO dimer portion can have a number average molecular weight from about 120 g/mol to about 600 g/mol.

The intermediate PAO dimer portion can possess at least one carbon-carbon unsaturated double bond. A portion of this intermediate PAO dimer can include tri-substituted vinylene. The tri-substituted vinylene can have possible isomer structures that may coexist and differ regarding where the unsaturated double bond is located, as represented by the following structure:

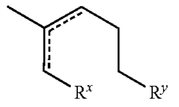

wherein the dashed line represents the two possible locations where the unsaturated double bond may be located and $R^x$ and $R^y$ are independently selected from a $C_3$ to $C_{21}$ alkyl group, such as from linear $C_3$ to $C_{21}$ alkyl group. Although the cis-form of tri-substituted vinylene is shown above, the trans-form of tri-substituted vinylene is also contemplated for one or more embodiments of the present disclosure. In at least one embodiment, the tri-substituted vinylenes of a feed are predominantly of the trans-isomer.

In at least one embodiment, the intermediate PAO dimer contains greater than about 20 wt %, such as greater than about 25 wt %, such as greater than about 30 wt %, such as greater than about 40 wt %, such as greater than about 50 wt %, such as greater than about 60 wt %, such as greater than about 70 wt %, such as greater than about 80 wt % of tri-substituted vinylene dimer represented by the general structure above.

In at least one embodiment, $R^x$ and $R^y$ are independently $C_3$ to $C_{11}$ alkyl groups. In at least one embodiment, $R^x$ and $R^y$ are both $C_2$. In at least one embodiment, the intermediate PAO dimer comprises a portion of tri-substituted vinylene dimer that is represented by the following structure:

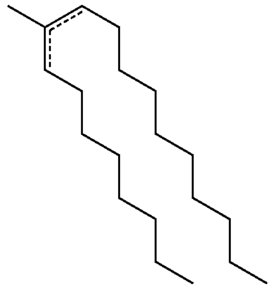

wherein the dashed line represents the two possible locations where the unsaturated double bond may be located.

In at least one embodiment, the intermediate PAO contains less than about 90 wt %, such as less than about 70 wt %, such as less than about 60 wt %, such as less than about 50 wt %, such as less than about 40 wt %, such as less than about 30 weight %, such as less than about 20 wt % of di-substituted vinylidene represented by the formula:

$R^qR^zC{=}CH_2$ wherein $R^q$ and $R^z$ are independently selected from alkyl groups, such as linear alkyl groups, such as $C_3$ to $C_{21}$ linear alkyl groups.

In at least one embodiment, the intermediate PAO product has a kinematic viscosity at 100° C. (KV100) of less than 20 cSt, such as less than 15 cSt, such as less than 12 cSt, such as less than 10 cSt, as determined by ASTM D445. The intermediate PAO trimer portion (after a hydrogenation process) can have a KV100 of less than 4 cSt, such as less than 3.6 cSt. In at least one embodiment, the tetramers and higher oligomer portion of the intermediate PAO (after a hydrogenation process) has a KV100 of less than 30 cSt. In at least one embodiment, the intermediate PAO oligomer portion remaining after the intermediate PAO dimer portion has a KV100 of less than 25 cSt.

The intermediate PAO trimer portion can have a viscosity index (VI) of greater than 125, such as greater than 130, as determined by ASTM D2270. In at least one embodiment, the trimer and higher oligomer portion of the intermediate PAO has a VI of greater than 130, such as greater than 135. In at least one embodiment, the tetramer and higher oligomer portion of the intermediate PAO has a VI of greater than 150, such as greater than 155.

The intermediate PAO trimer portion can have a Noack volatility that is less than 15 wt %, such as less than 14 wt %, such as less than 13 wt %, such as less than 12 wt %, as determined by ASTM D5800. In at least one embodiment, the intermediate PAO tetramers and higher oligomer portion has a Noack volatility that is less than 8 wt %, such as less than 7 wt %, such as less than 6 wt %.

In at least one embodiment, the dimer portion of the intermediate PAO may be a reactor effluent that is sent for further processing, such as that described below.

First Gas Chromatographic Measurement

In some embodiments, a process for producing poly alpha olefins includes measuring by gas chromatography an amount of one or more of vinylidene dimers and/or trisubstituted dimers (such as cis-trisubstituted dimers and trans-trisubstituted dimers). A sample (such as an intermediate PAO) may be removed from an apparatus (reactor) and introduced to a gas chromatograph. A gas chromatograph can separate the sample into individual components (also referred to as "fractions") and can provide a gas chromatography spectrum (also referred to as a "gas chromatogram") illustrating relative amounts (if present) of alpha olefin monomers, vinylidene dimers, trisubstituted dimers, trimers and higher oligomers (such as tetramers) present in the sample. In at least one embodiment, a process includes removing a sample from (1) the first reactor, (2) a line coupling the first reactor to a distillation unit, (3) a line coupling the first reactor to a filtration unit, or (4) a combination thereof. The process includes introducing the sample to a gas chromatograph.

A gas chromatograph can be any suitable gas chromatograph and may be obtained commercially, such as an Agilent 5975C GCMS (Gas Chromatograph Mass Spectrometer).

Tri-substituted olefin dimers provide higher selectivity (than vinylidene dimers) to trimers in an oligomerization process. Isomerization of vinylidene dimers to tri-substituted olefin dimers provides higher overall yields of trimers. Therefore, it can be beneficial to quickly determine dimer production to provide substantially real-time information during a process of the present disclosure. Quick determination of dimer production can provide determination of dimer production in commercial scale poly alpha olefin production processes, such as production processes of low viscosity poly alpha olefins. For example, a gas chromatography process might be performed in less than 20 minutes whereas a $C^{13}$ NMR process typically take 10 hours or more. Furthermore, a sample can be removed from an apparatus (reactor) and introduced to the gas chromatograph without modification or work up before introduction to the gas chromatograph (unlike NMR where a sample would be removed from the apparatus (reactor) and the sample would be extracted and dried before preparing an NMR sample for introduction into an NMR spectrometer).

In addition, it has been discovered that gas chromatography can discern cis-trisubstituted dimers from trans-trisubstituted dimers (e.g., a gas chromatography spectrum can illustrate separate elution profiles for cis-trisubstituted dimers and trans-trisubstituted dimers). In at least one embodiment, an intermediate PAO includes a molar ratio of cis-trisubstituted dimers to trans-trisubstituted dimers of from about 10:1 to about 1:10, such as from about 3:7 to about 7:3, such as about 4:6 to about 6:4, such as about 1:1. In at least one embodiment, an isomerized product includes a molar ratio of cis-trisubstituted dimers to trans-trisubstituted dimers of from about 10:1 to about 1:10, such as from about 3:7 to about 7:3, such as about 4:6 to about 6:4, such as about 1:1.

In some embodiments, an amount of one or more of vinylidene dimers and/or trisubstituted dimers can be measured during an trimer production process of the present disclosure using (1) a gas chromatograph coupled with the line transporting the vinylidene dimers from the first reactor to the filtration unit and/or the distillation unit, and/or (2) the gas chromatograph (or a different gas chromatograph) coupled with the line transporting vinylidene dimer from the distillation unit to the second reactor.

Measuring by gas chromatography may be used to determine whether (1) reactor conditions in the first reactor should be adjusted to promote dimer formation, (2) distillation conditions (e.g., cut point) of a distillation unit should be adjusted, and/or (3) heating should be provided to a line transferring effluent from the first reactor and/or transferring effluent from a distillation unit to the second reactor.

A gas chromatograph of the present disclosure can be optionally coupled with a mass spectrometer to provide molecular weight determination of one or more fractions eluted from the gas chromatograph. A fraction eluted from a gas chromatograph can be transferred to a mass spectrometer, and the mass spectrometer can then determine the molecular weight of the fraction. Mass spectrometers can be any suitable mass spectrometer and may be obtained commercially, such as an Agilent 5975C GCMS (Gas Chromatograph Mass Spectrometer).

In some embodiments, measuring by gas chromatography includes injecting a sample into an inlet device connected to the inlet of a column to perform a separation (forming fractions). Sample injection may be by any suitable sample injection device such as a syringe. The sampling device may hold a single sample or may hold multiple samples for injection into the column. The column can contain a stationary phase that can be the column coating material. The column may be coated with a non-polar material. For example, when the column coating material is methyl silicon polymer, the polarity can be measured by the percentage of methyl group substituted by the phenyl group. The polarity of coating materials are measured on a % of phenyl group substitution scale from 0 to 100 with zero being non-polar and 80 (80% phenyl substitution) being considered as polar. These methyl silicon polymers are considered non-polar and have polarity values in the range from 0 to 20. Phenyl substituted methyl silicon polymers are considered semi-polar and have polarity values of 21 to 50. Phenyl substituted methyl silicon polymers coating materials have been called polar materials when greater than 50% phenyl substitution group is included in polymers. In addition, a series of Carborane Silicon polymers sold under the trade name Dexsil have been especially designed for high temperature applications.

The column coated with a non-polar material provides a separation of the sample. The separation generates a series of bands (fractions) over a given time period. The bands represent individual components or groups of components of the sample injected, and separated or partially overlapping with adjacent bands.

A modulator can manage the flow and separation timing between the end of the column and the mass spectrometer. A modulator may be a thermal modulator that uses a trap/release mechanism. In this mechanism, cold nitrogen gas can be used to trap a separated fraction from the gas chromatograph followed by a periodic pulse of hot nitrogen to release trapped fraction to the mass spectrometer. Each pulse is analogous to a sample injection into the mass spectrometer. The role of the modulator is (1) collect the continuous eluent flow out from the end of the column with a fixed period of time (modulated period), and (2) inject collected eluent to the beginning of the mass spectrometer by releasing collected eluent at the end of modulated period. The function of the modulator is to define the beginning time of an injection into the mass spectrometer.

In some embodiments, measuring by gas chromatography includes withdrawing a sample from an apparatus (reactor). The sample can be from about 20 milligrams to about 100 milligrams, for example about 50 milligrams. The sample can be added to a standard auto-sampler vial (e.g., 2 milliliter vial) and diluted with a solvent, such as methylene chloride solvent. Vials can be sealed with septum caps. Samples can be run using an Agilent 5975C GCMS equipped with an auto-sampler. The GC column can be any suitable GC column, such as a Restek Rxi-1 ms. The column dimensions can be from about 30 meters to about 100 meters in length (such as about 60 meters)×0.1 mm to 0.5 mm internal diameter (such as about 0.25 mm) with a film thickness of from about 0.1 micron to about 1 micron film thickness (such as about 0.25 micron) for the stationary phase coating. A column flow rate can be from about 0.5 mL/min to about 5 mL/min (such as about 2 mL/min). The GC column can be connected to a split/split-less injection port (e.g., held at a temperature from about 250° C. to about 350° C., such as about 280° C., and operated in split mode; 125:1) of the GC. Helium in constant pressure mode can be used for GC carrier phase (e.g., a pressure from about 2 PSI to about 20 PSI, such as about 7 PSI). The outlet of the GC column can be run into the mass spectrometer via a transfer line held at 280° C. The temperature program for the GC column may be:

(1) providing a first temperature of from about 30° C. to about 100° C. (such as about 60° C.), (2) holding the first temperature for a time of from about 30 seconds to about 10 minutes, such as about 1 minute, (3) increasing the first temperature to a second temperature at a rate from about 2° C. per minute to about 20° C. per minute (such as about 10° C. per minute) and the second temperature is from about 60° C. to about 250° C., such as about 180° C., (4) holding the second temperature for a time from about 30 seconds to about 20 minutes, such as about 5 minutes, and (5) increasing the second temperature to a third temperature at a rate from about 10° C. per minute to about 40° C. per minute, such as about 25° C. per minute, and the third temperature is from about 200° C. to about 350° C., such as about 250° C. and (6) holding the third temperature for a time from about 30 seconds to about 30 minutes, such as about 8 minutes.

The mass spectrometer can be operated using an electron impact ionization source (e.g., hold at 250° C.) and operated using standard conditions (70 eV ionization). A detector temperature can be about 280° C. Instrumental control and mass spectral data acquisition can be obtained using Agilent Chemstation software. Mass calibration and instrument tuning performance can be validated using vendor supplied standard based on an instrument's auto tune feature.

GCMS retention times for samples can be determined relative to a normal paraffin or olefin retention based on analysis of standard sample containing known normal paraffins/olefins. Then the mass spectrum can be averaged.

In at least one embodiment, a GCMS is a gas chromatograph with field ionization time-of-flight mass spectrometer (GC-FI-TOF-MS). Field ionization time-of-flight mass spectrometry (FI-TOF-MS) characterizes the material exiting from the gas chromatogram.

Because gas chromatography can generally be used to separate hydrocarbon species by boiling point or polarity depending on type of column used, for GC-FI-TOF-MS, a gas chromatography technique for separation based on boiling point can be selected.

In the various types of mass spectrometry, a compound is detected by forming some type of ion. In field ionization, ions are formed by applying a high electric potential to a sharp surface. This results in an electric field near the surface that is suitable for forming ions of compounds, such as hydrocarbon compounds, that are on or near the surface. Field ionization is a process for forming ions that allows for "soft" ionization of hydrocarbon molecules. This means that the amount of fragmentation of hydrocarbon molecules due to the ionization is reduced or minimized. By using a soft ionization process, the number of peaks in the resulting mass spectrogram is reduced, which facilitates identification of compounds.

The compounds ionized by the field ionization are then detected using a time-of-flight mass spectrometer (TOF-MS). In various aspects, the time-of-flight mass spectrometer apparatus has sufficient resolution (mass resolving power>5000) to determine masses of hydrocarbons within 3 mDa or less, which allows for accurate determination of the elemental composition of a fraction. This also allows the TOF-MS apparatus to distinguish between species that differ in mass by only a few mDa. As a result, molecules that share the same nominal mass but differ in exact masses can be resolved. For molecules with identical chemical compositions, such as normal paraffins versus isoparaffins or olefins versus cycloparaffins, resolution of distinct species can be dependent on the retention time in the GC separation. TOF MS also accurately determines the masses of the hydrocarbon components (with an error of less than 3 mDa).

First Isomerization

Distinct from the oligomerization described above, after the olefin monomers are oligomerized, the resulting intermediate PAO (comprising vinylidene dimers) may be subjected to isomerization to form an isomerized product (comprising tri-substituted olefin dimers, e.g., tri-substituted vinylene dimers).

It has been discovered that vinylidene dimers (of the intermediate PAO) can be isomerized in the absence of added isomerization catalyst, rendering isomerization in an additional reactor merely optional. A heat exchanger can be coupled with a line transporting the intermediate PAO (comprising vinylidene dimers) from a first reactor to a filtration unit and/or to a distillation unit. The heat exchanger can provide heat to the intermediate PAO to promote isomerization of vinylidene dimers as they flow through the line transporting the intermediate PAO to form an isomerized product that is transferred through the line to the filtration unit and/or the distillation unit. Isomerizing vinylidene dimers in the absence of added isomerization catalyst (and/or in the absence of an isomerization reactor) provides substantial cost savings and throughput enhancement as compared to conventional poly alpha olefin processes. Furthermore, isomerizing vinylidene dimers in the absence of added isomerization catalyst renders merely optional a filtration unit coupled with the first reactor, as described in more detail below.

Isomerization is distinct from the oligomerization as the isomerization reaction does not result in two or more of the individual monomers or polymers bonding together, but is instead a rearrangement of the structure of the product; e.g., movement of double bonds or branching locations of the product.

In at least one embodiment, the isomerized product contains greater than 45 wt %, 50 wt % of tri-substituted vinylene dimer represented by the general structure above, such as greater than 55 wt %, such as greater than 60 wt %, such as greater than 65 wt %, such as greater than 75 wt %, such as greater than 85 wt %, such as greater than 90 wt %, such as greater than 95 wt %.

In at least one embodiment, the isomerized product contains less than 70 wt % of di-substituted vinylidene, such as less than 40 wt %, such as less than 30 wt %, such as less than 20 wt %, such as less than 10 weight %, such as less than 5 wt %.

The isomerization conditions, such as temperature and pressure, can depend upon the feed stock employed and the desired pour point of the product produced. Isomerization can be performed at a temperature from about 150° C. to about 475° C. In at least one embodiment, isomerization is performed at a temperature from about 200° C. to about 450° C., such as from about 200° C. to about 270° C. The temperature can be controlled using one or more heat exchangers, such as a heat jacket, coupled with a line as the intermediate PAO flows through the line.

A pressure used for isomerization may be from about 0.07 MPa to about 13.8 MPa (1 psi to 2,000 psi). In at least one embodiment, the pressure is from about 0.07 MPa to about 6.89 MPa (10 psi to 1,000 psi), such as about 0.69 MPa to 4.14 MPa (100 psi to 600 psi).

The pressure used for isomerization can be controlled using flow rates of the intermediate PAO (as a first reactor effluent) through a line to a subsequent processing unit (such as a filtration unit or distillation unit). For example, a higher flow rate of intermediate PAO through a line promotes a higher pressure experienced by the intermediate PAO in the line, as compared to a lower flow rate through the line. In at least one embodiment, a flow rate of intermediate PAO through a line is from about 1 lb/min to about 5,000 lbs/min, such as from about 30 lbs/min. to about 300 lbs/min.

The pressure and flow rate can be controlled using one or more pumps coupled with a line as the intermediate PAO flows through the line.

Filtration

The intermediate PAO or isomerized product can be transferred via a line to a filtration unit. It has been discovered that, in embodiments using an isomerized product, for example, the isomerized product can be filtered through a less expensive and less complex filtration unit (instead of a conventional cellulosic body feed-type filtration unit) which provides additional cost savings and throughput enhancement. Cellulosic body feed-type filtration units can be those having a cellulosic body feed-type filter which has polar groups (e.g., hydroxyl groups) that couple with contaminants in the feed through the filtration unit.

Alternatively, in embodiments using an isomerized product, for example, a filtration unit is merely optional and the isomerized product can be transferred from the first reactor to a distillation unit or the second reactor. Because filtration can be bypassed completely, overall throughput enhancement of end products is achieved.

Filtration units of the present disclosure can include crude particulate filters, such as a particulate filter having a large pore size. Particulate filters can include a cartridge filter, a cellulosic cartridge filter, bag filter, or other filtration device, and/or can have an average pore size of from about 0.1 micron to about 100 microns.

Because filters having large pore sizes can be used, flow rates of isomerized product (or intermediate PAO) through filtration units of the present disclosure can be greater than flow rates used for conventional cellulosic body feed-type filtration units. Because flow rates of isomerized product (or intermediate PAO) through filtration units of the present disclosure can be greater than conventional flow rates, overall throughput enhancement of end products is achieved.

In at least one embodiment, a flow rate of isomerized product (or intermediate PAO) through a filtration unit is from about 1 lb/min. to about 5,000 lbs/min, such as from about 10 lbs/min. to about 300 lbs/min.

After filtration, a filtration effluent can be transferred to one or more distillation units and/or to a second reactor.

Distillation

In at least one embodiment, the intermediate PAO, isomerized product, and/or filtration effluent may be subjected to a distillation process to (1) remove water and other light byproducts and/or impurities, and (2) separate dimers (and unreacted alpha olefin monomers, if any) from the trimers and higher oligomers (if any). Any suitable distillation unit can be used for distillations of the present disclosure. In at least one embodiment, removal of water and other light byproducts and/or impurities is performed in a first distillation unit to form a first distillation effluent having dimers, trimers, and higher oligomers (if any). The first distillation effluent can be transferred to a second distillation unit for separation of dimers (and unreacted alpha olefin monomers, if any) from the trimers and higher oligomers (if any). The second distillation unit can form (1) a second distillation effluent having dimers (and unreacted alpha olefin monomers, if any) and (2) a third distillation effluent having trimers and higher oligomers (if any). The third distillation effluent can be transferred to a hydrogenation reactor, for example as described in more detail below. The second distillation effluent can be transferred to a second reactor (e.g., a second oligomerization reactor) and can optionally undergo an isomerization process before entering the second reactor. Performing an isomerization process on the second distillation effluent can be performed (1) in embodiments where a first isomerization process has not been performed (e.g., a first isomerization process described above) or (2) in addition to a first isomerization process of vinylidene dimers (e.g., as described above).

In at least one embodiment, a distillation unit is configured to remove water and other light byproducts and/or impurities from a feed. The distillation unit can be operated at a cut point of from about 50° C. to about 400° C. at a pressure of from about 0.1 mmHg to 760 mmHg, such as about 150° C. to about 275° C. at a pressure of from about 1 mmHg to about 50 mmHg.

In at least one embodiment, a distillation unit is configured to separate dimers (and unreacted alpha olefin monomers, if any) from trimers and higher oligomers (if any). The distillation unit can be operated at a cut point of from about 50° C. to about 400° C. at a pressure of from about 0.1 mmHg to 760 mmHg, such as about 200° C. to about 300° C. at a pressure of from about 1 mmHg to about 20 mmHg.

Second Isomerization

A distillation effluent having vinylidene dimers may be subjected to isomerization to form an isomerized product (e.g., a second isomerized product) comprising tri-substituted olefin dimers, e.g., tri-substituted vinylene dimers). A second isomerization can be performed instead of, or in addition to, a first isomerization of the intermediate PAO.

Distillation effluent can be, for example, a distillation effluent of a second distillation unit (e.g., as described above).

It has been discovered that vinylidene dimers (of a distillation effluent) can be isomerized in the absence of added isomerization catalyst, rendering isomerization in an additional reactor merely optional. Accordingly, a heat exchanger can be coupled with a line transporting the distillation effluent (comprising vinylidene dimers) from a distillation unit to a second reactor (e.g., a second oligomerization reactor). Isomerizing vinylidene dimers in the absence of added isomerization catalyst (and/or in the absence of an isomerization reactor) provides substantial cost savings and throughput enhancement, as compared to conventional poly alpha olefin processes. Without being bound by theory, it is believed that there may be one or more unidentified catalytic species present in the intermediate PAO and distillation effluent that can catalyze the isomerization reaction(s). If so, the catalytic species likely has/have a comparable boiling point as the boiling point of vinylidene dimers and/or tri-substituted olefin dimers.

In at least one embodiment, an isomerized product (e.g., a second isomerized product) contains greater than 50 wt %, such as greater than 55 wt %, such as greater than 60 wt %, such as greater than 65 wt %, such as greater than 75 wt %, such as greater than 85 wt %, such as greater than 90 wt %, such as greater than 95 wt % of tri-substituted vinylene dimer represented by the general structure above.

In at least one embodiment, an isomerized product (e.g., a second isomerized product) contains less than 70 wt %, such as less than 40 wt %, such as less than 30 wt %, such as less than 20 wt %, such as less than 10 weight %, such as less than 5 wt % of di-substituted vinylidene.

The isomerization conditions, such as temperature and pressure, can depend upon the feed stock employed and the desired pour point of the product produced. Isomerization can be performed at a temperature from about 150° C. to about 475° C. In at least one embodiment, isomerization is performed at a temperature from about 200° C. to about 450° C., such as from about 200° C. to about 270° C. The temperature can be controlled using one or more heat exchangers, such as a heat jacket, coupled with a line as the distillation effluent flows through the line.

A pressure used for isomerization may be from about 0.07 MPa to about 13.8 MPa (1 psi to 2,000 psi). In at least one embodiment, the pressure is from about 0.07 MPa to about 6.89 MPa (10 psi to 1,000 psi), such as about 0.69 MPa to 4.14 MPa (100 psi to 600 psi).

The pressure used for isomerization can be controlled using flow rates of the distillation effluent through a line to a subsequent processing unit (such as a second oligomerization reactor). For example, a higher flow rate of distillation effluent through a line promotes a higher pressure experienced by the distillation effluent in the line, as compared to a lower flow rate through the line. In at least one embodiment, a flow rate of distillation effluent through a line is from about 5 lbs/min. to about 1,000 lbs/min., such as from about 10 lbs/min. to about 300 lbs/min.

The pressure and flow rate can be controlled using one or more pumps coupled with a line as the distillation effluent flows through the line.

Second Gas Chromatographic Measurement

In some embodiments, a process for producing poly alpha olefins includes measuring by gas chromatography an amount of one or more of vinylidene dimers and/or trisubstituted dimers (such as cis-trisubstituted dimers and trans-trisubstituted dimers). A "second" gas chromatographic measurement as used herein can be performed instead of or in addition to a "first" gas chromatographic measurement. For a second gas chromatographic measurement, a sample (such as a distillation effluent or filtration effluent) may be removed from an apparatus (reactor) and introduced to a gas chromatograph. A gas chromatograph can separate the sample into individual components (also referred to as "fractions") and can provide a gas chromatography spectrum (also referred to as a "gas chromatogram") illustrating relative amounts (if present) of alpha olefin monomers, vinylidene dimers, trisubstituted dimers, trimers and higher oligomers (such as tetramers) present in the sample. In at least one embodiment, a process includes removing a sample from (1) a line coupling a filtration unit to a distillation unit, (2) a line coupling a first distillation unit to a second distillation unit, (3) a line coupling a distillation unit to a second reactor, or (4) a combination thereof. The process includes introducing the sample to a gas chromatograph.

A gas chromatograph can be any suitable gas chromatograph and may be obtained commercially, such as an Agilent 5975C GCMS (Gas Chromatograph Mass Spectrometer).

Tri-substituted olefin dimers provide higher selectivity (than vinylidene dimers) to trimers in an oligomerization process. Isomerization of vinylidene dimers to tri-substituted olefin dimers provides higher overall yields of trimers. Therefore, it can be beneficial to quickly determine dimer production to provide substantially real-time information during a process of the present disclosure. Quick determination of dimer production can provide determination of dimer production in commercial scale poly alpha olefin production processes, such as production processes of low viscosity poly alpha olefins. For example, a gas chromatography process might be performed in less than 20 minutes whereas a $C^{13}$ NMR process typically take 10 hours or more. Furthermore, a sample can be removed from an apparatus (reactor) and introduced to the gas chromatograph without modification or work up before introduction to the gas chromatograph (unlike NMR where a sample would be removed from the apparatus (reactor) and the sample would be extracted and dried before preparing an NMR sample for introduction into an NMR spectrometer).

In addition, it has been discovered that gas chromatography can discern cis-trisubstituted dimers from trans-trisubstituted dimers (e.g., a gas chromatography spectrum can illustrate separate elution profiles for cis-trisubstituted dimers and trans-trisubstituted dimers). In at least one embodiment, a distillation effluent includes a molar ratio of cis-trisubstituted dimers to trans-trisubstituted dimers of from about 10:1 to about 1:10, such as from about 3:7 to about 7:3, such as about 4:6 to about 6:4, such as about 1:1. In at least one embodiment, an isomerized product (e.g., a second isomerized product) includes a molar ratio of cis-trisubstituted dimers to trans-trisubstituted dimers of from about 10:1 to about 1:10, such as from about 3:7 to about 7:3, such as about 4:6 to about 6:4, such as about 1:1.

In some embodiments, an amount of one or more of vinylidene dimers and/or trisubstituted dimers can be measured during an trimer production process of the present disclosure using (1) a gas chromatograph coupled with a line transporting tri-substituted vinylene dimer from a filtration unit to a distillation unit, (2) the gas chromatograph (or a different gas chromatograph) coupled with a line transporting tri-substituted vinylene dimer from a first distillation unit to a second distillation unit, and/or (3) the gas chromatograph (or a different gas chromatograph) coupled with a line transporting tri-substituted vinylene dimer from a distillation unit to a second reactor.

Measuring by gas chromatography may be used to determine whether (1) reactor conditions in the first reactor should be adjusted to promote dimer formation, (2) distillation conditions (e.g., cut point) of a distillation unit should be adjusted, and/or (3) heating should be provided to a line transferring effluent from the first reactor and/or transferring effluent from a distillation unit to the second reactor.

A gas chromatograph of the present disclosure can be optionally coupled with a mass spectrometer to provide molecular weight determination of one or more fractions eluted from the gas chromatograph. A fraction eluted from a gas chromatograph can be transferred to a mass spectrometer, and the mass spectrometer can then determine the molecular weight of the fraction. Mass spectrometers can be any suitable mass spectrometer and may be obtained commercially, such as an Agilent 5975C GCMS (Gas Chromatograph Mass Spectrometer).

In some embodiments, measuring by gas chromatography includes injecting a sample into an inlet device connected to the inlet of a column to perform a separation (forming fractions). Sample injection may be by any suitable sample injection device such as a syringe. The sampling device may hold a single sample or may hold multiple samples for injection into the column. The column can contain a stationary phase that can be the column coating material. The column may be coated with a non-polar material. For example, when the column coating material is methyl silicon polymer, the polarity can be measured by the percentage of methyl group substituted by the phenyl group. The polarity of coating materials are measured on a % of phenyl group substitution scale from 0 to 100 with zero being non-polar and 80 (80% phenyl substitution) being considered as polar. These methyl silicon polymers are considered non-polar and have polarity values in the range from 0 to 20. Phenyl substituted methyl silicon polymers are considered semi-polar and have polarity values of 21 to 50. Phenyl substituted methyl silicon polymers coating materials have been called polar materials when greater than 50% phenyl substitution group is included in polymers. In addition, a series of Carborane Silicon polymers sold under the trade name Dexsil have been especially designed for high temperature applications.

The column coated with a non-polar material provides a separation of the sample. The separation generates a series of bands (fractions) over a given time period. The bands represent individual components or groups of components of the sample injected, and separated or partially overlapping with adjacent bands.

A modulator can manage the flow and separation timing between the end of the column and the mass spectrometer. A modulator may be a thermal modulator that uses a trap/release mechanism. In this mechanism, cold nitrogen gas can be used to trap a separated fraction from the gas chromatograph followed by a periodic pulse of hot nitrogen to release trapped fraction to the mass spectrometer. Each pulse is analogous to a sample injection into the mass spectrometer. The role of the modulator is (1) collect the continuous eluent flow out from the end of the column with a fixed period of time (modulated period), and (2) inject collected eluent to the beginning of the mass spectrometer by releasing collected eluent at the end of modulated period. The function of the modulator is to define the beginning time of an injection into the mass spectrometer.

In some embodiments, measuring by gas chromatography includes withdrawing a sample from an apparatus (reactor). The sample can be from about 20 milligrams to about 100 milligrams, for example about 50 milligrams. The sample can be added to a standard auto-sampler vial (e.g., 2 milliliter vial) and diluted with a solvent, such as methylene chloride solvent. Vials can be sealed with septum caps. Samples can be run using an Agilent 5975C GCMS equipped with an auto-sampler. The GC column can be any suitable GC column, such as a Restek Rxi-1 ms. The column dimensions can be from about 30 meters to about 100 meters in length (such as about 60 meters)×0.1 mm to 0.5 mm internal diameter (such as about 0.25 mm) with a film thickness of from about 0.1 micron to about 1 micron film thickness (such as about 0.25 micron) for the stationary phase coating. A column flow rate can be from about 0.5 mL/min to about 5 mL/min (such as about 2 mL/min). The GC column can be connected to a split/split-less injection port (e.g., held at a temperature from about 250° C. to about 350° C., such as about 280° C., and operated in split mode; 125:1) of the GC. Helium in constant pressure mode can be used for GC carrier phase (e.g., a pressure from about 2 PSI to about 20 PSI, such as about 7 PSI). The outlet of the GC column can be run into the mass spectrometer via a transfer line held at 280° C. The temperature program for the GC column may be:

(1) providing a first temperature of from about 30° C. to about 100° C. (such as about 60° C.),
(2) holding the first temperature for a time of from about 30 seconds to about 10 minutes, such as about 1 minute,
(3) increasing the first temperature to a second temperature at a rate from about 2° C. per minute to about 20° C. per minute (such as about 10° C. per minute) and the second temperature is from about 60° C. to about 250° C., such as about 180° C.,
(4) holding the second temperature for a time from about 30 seconds to about 20 minutes, such as about 5 minutes, and
(5) increasing the second temperature to a third temperature at a rate from about 10° C. per minute to about 40° C. per minute, such as about 25° C. per minute, and the third temperature is from about 200° C. to about 350° C., such as about 250° C. and
(6) holding the third temperature for a time from about 30 seconds to about 30 minutes, such as about 8 minutes.

The mass spectrometer can be operated using an electron impact ionization source (e.g., hold at 250° C.) and operated using standard conditions (70 eV ionization). A detector temperature can be about 280° C. Instrumental control and mass spectral data acquisition can be obtained using Agilent Chemstation software. Mass calibration and instrument tuning performance can be validated using vendor supplied standard based on an instrument's auto tune feature.

GCMS retention times for samples can be determined relative to a normal paraffin or olefin retention based on analysis of standard sample containing known normal paraffins/olefins. Then the mass spectrum can be averaged.

In at least one embodiment, a GCMS is a gas chromatograph with field ionization time-of-flight mass spectrometer (GC-FI-TOF-MS). Field ionization time-of-flight mass spectrometry (FI-TOF-MS) characterizes the material exiting from the gas chromatogram.

Because gas chromatography can generally be used to separate hydrocarbon species by boiling point or polarity depending on type of column used, for GC-FI-TOF-MS, a gas chromatography technique for separation based on boiling point can be selected.

In the various types of mass spectrometry, a compound is detected by forming some type of ion. In field ionization, ions are formed by applying a high electric potential to a sharp surface. This results in an electric field near the surface that is suitable for forming ions of compounds, such as hydrocarbon compounds, that are on or near the surface. Field ionization is a process for forming ions that allows for "soft" ionization of hydrocarbon molecules. This means that the amount of fragmentation of hydrocarbon molecules due to the ionization is reduced or minimized. By using a soft ionization process, the number of peaks in the resulting mass spectrogram is reduced, which facilitates identification of compounds.

The compounds ionized by the field ionization are then detected using a time-of-flight mass spectrometer (TOF-MS). In various aspects, the time-of-flight mass spectrometer apparatus has sufficient resolution (mass resolving power>5000) to determine masses of hydrocarbons within 3 mDa or less, which allows for accurate determination of the elemental composition of a fraction. This also allows the TOF-MS apparatus to distinguish between species that differ in mass by only a few mDa. As a result, molecules that share the same nominal mass but differ in exact masses can be resolved. For molecules with identical chemical compositions, such as normal paraffins versus isoparaffins or olefins versus cycloparaffins, resolution of distinct species can be dependent on the retention time in the GC separation. TOF MS also accurately determines the masses of the hydrocarbon components (with an error of less than 3 mDa).

Second Oligomerization

The intermediate PAO from the first oligomerization (or a filtration effluent or a distillation effluent) may be used as the sole olefin feedstock to the subsequent oligomerization or may be used together with an alpha olefin feedstock of the type used as the olefin starting material for the first oligomerization. Other portions of the effluent from the first oligomerization may also be used as a feedstock to the subsequent oligomerization, including unreacted LAO. The intermediate PAO dimer may suitably be separated from the overall intermediate PAO product by distillation (e.g., as described above), with the cut point set at a value dependent upon the fraction to be used as lube base stock or the fraction to be used as feed for the subsequent oligomerization. Alpha olefins with the same attributes as those used for the first oligomerization may be used for the second oligomerization. Typically molar ratios for the intermediate PAO dimer fraction (or filtration effluent or distillation effluent) to the alpha olefins fraction in the feedstock are from about 90:10 to about 10:90, such as from about 80:20 to about 20:80 by weight. In at least one embodiment, the intermediate PAO dimer (or filtration effluent or distillation effluent) will make up around 50 mole % of the olefinic feed material since the properties and distribution of the final product, dependent in part upon the starting material, can be favorably affected by feeding the intermediate PAO dimer (or filtration effluent or distillation effluent) at an equimolar ratio with the alpha olefins. Temperatures for the subsequent oligomerization in the second reactor can be from about 15° C. to about 60° C.

Any suitable oligomerization process and catalyst may be used for the subsequent oligomerization. A catalyst for the subsequent oligomerization can be a non-transition metal catalyst. A catalyst can be a Lewis acid catalyst. Patent applications US 2009/156874 and US 2009/240012 describe a process for the subsequent oligomerization, to which reference is made for details of feedstocks, compositions, catalysts and co-catalysts, and process conditions. The Lewis acid catalysts of US 2009/156874 and US 2009/240012 include the metal and metalloid halides conventionally used as Friedel-Crafts catalysts, examples include $AlCl_3$, $BF_3$, $AlBr_3$, $TiCl_3$, and $TiCl_4$ either alone or with a protic promoter/activator. Boron trifluoride is commonly used but not particularly suitable unless it is used with a protic promoter. Useful co-catalysts are well known and described in detail in US 2009/156874 and US 2009/240012. Solid Lewis acid catalysts, such as synthetic or natural zeolites, acid clays, polymeric acidic resins, amorphous solid catalysts such as silica-alumina, and heteropoly acids such as the tungsten zirconates, tungsten molybdates, tungsten vanadates, phosphotungstates and molybdotungstovanadogermanates (e.g., WOx/$ZrO_2$, WOx/$MoO_3$) may also be used although these are not generally as favored economically. Additional process conditions and other details are described in detail in US 2009/156874 and US 2009/240012, and incorporated herein by reference.

In at least one embodiment, the subsequent oligomerization is performed in the presence of $BF_3$ and at least two different activators selected from alcohols and alkyl acetates. The alcohols are C1 to C10 alcohols and the alkyl acetates are C1 to C10 alkyl acetates. For example, both co-activators are C1 to C6 based compounds. Two example combinations of co-activators are i) ethanol and ethyl acetate and ii) n-butanol and n-butyl acetate. The ratio of alcohol to alkyl acetate can be from about 0.2 to about 15, such as from about 0.5 to about 7.

The structure of the intermediate PAO (or filtration effluent or distillation effluent) is such that, when reacted in a subsequent oligomerization, the intermediate PAO (or filtration effluent or distillation effluent) reacts preferentially with the optional LAO to form a co-dimer of the dimer and LAO at high yields. This allows for high conversion and yield rates of the PAO products. In at least one embodiment, the PAO product from the subsequent oligomerization comprises primarily a co-dimer (e.g., a trimer) formed from the dimer and the respective LAO feedstock. In at least one embodiment, where the LAO feedstock for both oligomerization processes is 1-decene, the incorporation of intermediate Cm PAO dimer into higher oligomers can be greater than about 80%, such as greater than about 90%, the conversion of the LAO can be greater than about 95%, such as greater than about 99%, and/or the yield % of C30 product in the overall product mix can be greater than about 75%, such as greater than about 90%. In another embodiment, where the LAO feedstock is 1-octene, the incorporation of the intermediate PAO dimer into higher oligomers can be greater than about 80%, such as greater than about 90%, the conversion of the LAO can be greater than about 95%, such as greater than about 99%, and/or the yield % of $C_{28}$ product in the overall product mix can be greater than 75%, such as greater than about 90%. In another embodiment, where the feedstock is 1-dodecene, the incorporation of the intermediate PAO dimer into higher oligomers can be greater than about 80%, such as greater than about 90%, the conversion of the LAO can be greater than about 95%, such as greater than about 99%, and/or the yield % of $C_{32}$ product in the overall product mix can be greater than about 75%, such as greater than about 90%.

In at least one embodiment, the monomer is optional as a feedstock in the second reactor. In some embodiments, the first reactor effluent comprises unreacted monomer, and the unreacted monomer is fed to the second reactor. In some embodiments, monomer is fed into the second reactor, and the monomer is an LAO selected from the group including 1-hexene, 1-octene, 1-nonene, 1-decene, 1-dodecene, and 1-tetradecene. In some embodiments, the PAO produced in the subsequent oligomerization is derived from the intermediate PAO dimer plus only one monomer. In some embodiments, the PAO produced in the subsequent oligomerization is derived from the intermediate PAO dimer plus two or more monomers, or three or more monomers, or four or more monomers, or even five or more monomers. For example, the intermediate PAO dimer plus a $C_8$, $C_{10}$, $C_{12}$-LAO mixture, or a $C_6$, $C_7$, $C_8$, $C_9$, $C_{10}$, $C_{11}$, $C_{12}$, $C_{13}$, $C_{14}$-LAO mixture, or a $C_4$, $C_6$, $C_8$, $C_{10}$, $C_{12}$, $C_{14}$, $C_{16}$, $C_{18}$-LAO mixture can be used as a feed. In some embodiments, the PAO produced in the subsequent oligomerization comprises less than 30 mole % of $C_2$, $C_3$ and $C_4$ monomers, such as less than 20 mole %, such as less than 10 mole %, such as less than 5 mole %, such as less than 3 mole %, such as 0 mole %. Specifically, in another embodiment, the PAO produced in the subsequent oligomerization comprises less than 30 mole % of ethylene, propylene and butene, such as less than 20 mole %, such as less than 10 mole %, such as less than 5 mole %, such as less than 3 mole %, such as 0 mole %.

The PAOs produced in the subsequent oligomerization may be a mixture of dimers, trimers, and optionally tetramer and higher oligomers. This PAO is referred to interchangeably as the "second reactor effluent." The properties of the isomerized product(s) of the present disclosure enable a high yield of a co-dimer (e.g., trimers) of tri-substituted vinylene dimers and LAO in the second reactor effluent. The PAOs in the second reactor effluent are notable because very low viscosity PAOs can be achieved at very high yields, and these PAOs can have excellent rheological properties, including low pour point, Noack volatility, and very high viscosity indexes.

In at least one embodiment, the PAOs of the second reactor effluent may contain trace amounts of transition metal compound if the catalyst in the first or subsequent oligomerization is a metallocene catalyst. A trace amount of transition metal compound may be any amount of transition metal compound or Group 4 metal present in the PAO. Presence of Group 4 metal may be detected at the ppm or ppb level by ASTM 5185.

The second reactor effluent PAO can have a portion having a carbon count of $C_{28}$-$C_{32}$, wherein the $C_{28}$-$C_{32}$ portion is at least about 65 wt %, such as at least about 70 wt %, such at least about 80 wt %, such as at least about 90 wt %, such as at least about 95 wt %, such as at least about 99 wt %, such as from about 70 wt % to about 99 wt %, such as from about 70 wt % to about 90 wt %, of the second reactor effluent.

The kinematic viscosity at 100° C. of the second reactor effluent PAO can be less than about 10 cSt, such as less than about 6 cSt, such as less than about 4.5 cSt, such as less than about 3.2 cSt, such as from about 2.8 to about 4.5 cSt. The kinematic viscosity at 100° C. of the $C_{28}$ portion of the PAO can be less than 3.2 cSt. In at least one embodiment, the kinematic viscosity at 100° C. of the $C_{28}$ to $C_{32}$ portion of the second reactor effluent PAO can be less than about 10 cSt, such as less than about 6 cSt, such as less than about 4.5 cSt, such as from about 2.8 to about 4.5 cSt.

In at least one embodiment, the pour point of the PAO is below about −40° C., such as below about −50° C., such as below about −60° C., such as below about −70° C., such as below about −80° C. The pour point of the $C_{28}$ to $C_{32}$ portion of the second reactor effluent PAO can be below −30° C., such as below about −40° C., such as below about −50° C., such as below about −60° C., such as below about −70° C., such as below about −80° C.

The Noack volatility of the second reactor effluent PAO may be not more than about 9.0 wt %, such as not more than about 8.5 wt %, such as not more than about 8.0 wt %, such as not more than about 7.5 wt %. The Noack volatility of the $C_{28}$ to $C_{32}$ portion of the second reactor effluent PAO may be less than about 19 wt %, such as less than about 14 wt %, such as less than about 12 wt %, such as less than about 10 wt %, such as less than about 9 wt %.

The viscosity index of the second reactor effluent PAO can be more than about 121, such as more than about 125, such as more than about 130, such as more than about 136. The viscosity index of the trimer or $C_{28}$ to $C_{32}$ portion of the second reactor effluent PAO can be above about 120, such as above about 125, such as above about 130, such as at least about 135.

The cold crank simulator value (CCS) at −25° C. of the second reactor effluent PAO or a portion of the second reactor effluent PAO may be not more than about 500 cP, such as not more than about 450 cP, such as not more than about 350 cP, such as not more than about 250 cP, such as from about 200 to about 450 cP, such as about 100 to about 250 cP.

In at least one embodiment, the second reactor effluent PAO has a kinematic viscosity at 100° C. of not more than about 3.2 cSt and a Noack volatility of not more than about 19 wt %. In another embodiment, the second reactor effluent PAO has a kinematic viscosity at 100° C. of not more than about 4.1 cSt and a Noack volatility of not more than about 9 wt %.

The ability to achieve such low viscosity PAOs with such low Noack volatility at such high yields is noteworthy, and attributable to the high tri-substituted vinylene dimer content (provided by one or more isomerization processes) of various feeds of the processes of the present disclosure. The tri-substituted vinylene dimers have properties that make them selectively reactive in the subsequent oligomerization process.

Hydrogenation

The second reactor effluent PAO from the subsequent oligomerization can be hydrogenated prior to use as a lubricant basestock to remove residual unsaturation and stabilize the product. An optional hydrogenation may be carried out in any suitable manner for hydrotreating conventional PAOs.

Hydrogenation may be performed in any suitable hydrogenation reactor. The catalyst employed in the isomerization reaction may saturate the second reactor effluent PAO.

Any conventional hydrogenation reaction may be employed in the present disclosure. For example, the hydrogenation process described in U.S. Pat. No. 4,125,569, which is incorporated herein by reference, may be employed. Hydrogenation catalysts include nickel on Kieselguhr catalyst and conventional metallic hydrogenation catalysts, for example, oxide, hydroxide, or free metal forms of the Group VIII metals, such as cobalt, nickel, palladium, and platinum. The metals can be associated with carriers such as bauxite, alumina, silica gel, silica-alumina composites, activated carbon, crystalline aluminosilicate zeolites, and clay. Also, non-noble Group VIII metals, metal oxides, and sulfides can be used. Additional examples of catalysts which may be employed in the hydrogenation reaction are disclosed in U.S. Pat. Nos. 3,852,207; 4,157,294; 3,904,513; and 4,673,487, which are incorporated herein by reference. The catalysts mentioned above may be employed separately or in combination with one another.

In the hydrogenation reaction, a slight excess to a large excess of hydrogen can be used. Unreacted hydrogen may be separated from the hydrogenated product and recycled to the hydrogenation reactor.

The hydrogenation reactor provides hydrogenated product effluent that can then be transferred to one or more distillation units to separate an ultra-low viscosity PAO (e.g., about 3 cST) from an intermediate viscosity PAO (e.g., about 6 cST) and any residual heavies present in the effluent.

Polyalphaolefin Product

The intermediate PAOs and PAOs produced (e.g., hydrogenated PAOs) by the processes of the present disclosure, particularly those of ultra-low viscosity, can be especially suitable for high performance automotive engine oil formulations either by themselves or by blending with other fluids, such as Group II, Group II+, Group III, Group III+ or lube basestocks derived from hydroisomerization of wax fractions from Fisher-Tropsch hydrocarbon synthesis from $CO/H_2$ syn gas, or other Group IV or Group V basestocks. They can be preferred grades for high performance industrial oil formulations that call for ultra-low and low viscosity oils. Additionally, they can be suitable for use in personal care applications, such as soaps, detergents, creams, lotions, shampoos, and detergents.

The PAO formed following hydrogenation ("hydrogenated PAO") may have a KV100 not greater than about 20 cSt. In at least one embodiment, the KV100 of the product can be from about 1 cSt to about 20 cSt, about 1.2 to about 15 cSt, about 1.5 to about 15 cSt, about 1.5 to about 10 cSt, about 3 to about 15 cSt, or about 3 to about 10 cSt. In some embodiments, the PAO has a KV100 of from about 1 to about 6, such as from about 1.2 to about 5, such as about 1.5 to about 5, such as about 3 to about 4. In some embodiments, the PAO has a maximum KV100 of 20, 18, 15, 10, or 8.

The hydrogenated PAOs can have a pour point of less than about −20° C. In some embodiments, the pour point is less than about −40° C., less than about −55° C., or less than about −60° C.

In at least one embodiment, the hydrogenated PAOs have a VI above about 100, such as above about 110, such as above about 120, such as above about 130, such as above about 140, such as above about 150. In at least one embodiment, the VI is from about 120 to about 145, such as about 120 to about 155, or about 120 to about 160.

Hydrogenated PAOs can have a KV100 of about 3 cSt or less with low pour points, which can be useful in the formulation of specialty, fuel/energy efficient transmission or hydraulic fluids. The low viscosity fluids having a KV100 of about 3 cSt may be useful as high performance fuel and/or energy efficient base stocks.

Examples of Configurations

FIG. 1 is a diagram illustrating an apparatus for carrying out certain aspects of the present disclosure according to at least one embodiment. More generally, a configuration shown in FIG. 1 or similar to FIG. 1 can be used for forming poly alpha olefins of the present disclosure.

As shown in FIG. 1, an apparatus 100 includes a feed line 102 coupled with a first reactor 104 (e.g., an oligomerization reactor). During use, a feed of feed line 102 can include an alpha olefin. First reactor 104 is coupled with a first distillation unit 106 via line 108. A first reactor effluent (including intermediate PAO) of line 108 is transferred to first distillation unit 106 where byproducts and/or contaminants can be separated from the first reactor effluent. The byproducts and/or contaminants may be removed as a tops fraction 150. First distillation unit 106 is coupled with a second distillation unit 110 via line 130. A gas chromatograph 134 is coupled with line 108. A sample may be removed from line 108 manually or using one or more valves (not shown) to direct, when in the open position, a portion of the first reactor effluent to gas chromatograph 134. A first distillation effluent (including intermediate PAO) of line 130 is transferred to second distillation unit 110. Second distillation unit 110 is coupled with a second reactor 116 (e.g., an oligomerization reactor) via line 118. A distillation effluent including dimers and unreacted monomers of line 118 is transferred to second reactor 116. A gas chromatograph 136 is coupled with line 118. A sample may be removed from line 118 manually or using one or more valves (not shown) to direct, when in the open position, a portion of the distillation effluent to gas chromatograph 136. Second distillation unit 110 is further coupled with a hydrogenation reactor 112 via line 114. A distillation effluent including trimers, tetramers, and higher oligomers (if any) of line 114 is transferred to the hydrogenation reactor 112. Second reactor 116 is coupled with the hydrogenation reactor 112 via line 132. An effluent of the second reactor (e.g., effluent including trimers) of line 132 is transferred to hydrogenation reactor 112. Alternatively, second reactor 116 can be coupled with a separate hydrogenation reactor (not shown) (e.g., not reactor 112). As shown in FIG. 1, hydrogenation reactor 112 is coupled with a third distillation unit 120 via line 122. A hydrogenated PAO product of line 122 is transferred to the third distillation unit 120 for separation into an ultra-low viscosity PAO (trimer) (removed by effluent line 126), a low to medium viscosity PAO (tetramer+) (removed by effluent line 128), and a lights fraction (dimer or lighter) (removed by effluent line 124).

Figure 2:
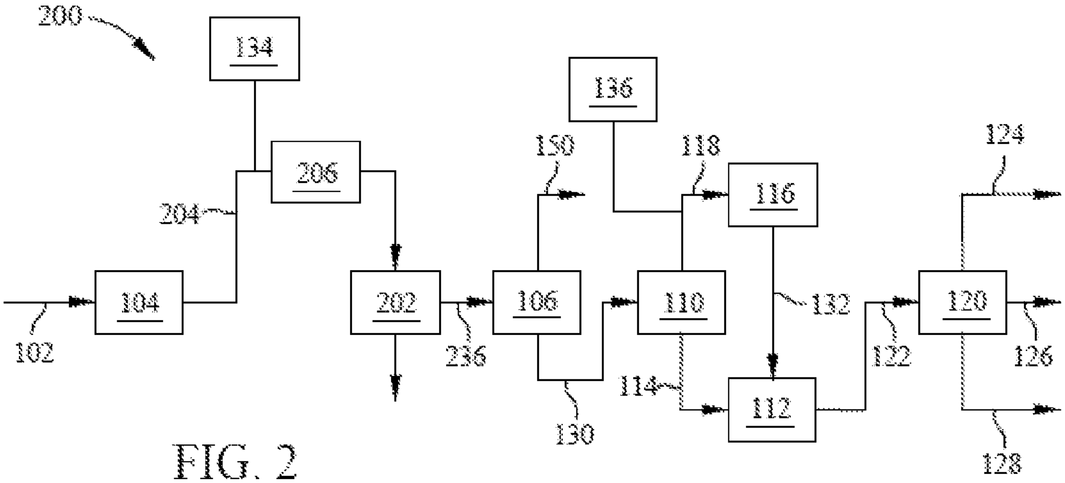
FIG. 2 is an apparatus for forming poly alpha olefins, according to at least one embodiment.

FIG. 2 is a diagram illustrating an apparatus for carrying out certain aspects of the present disclosure. More generally, a configuration shown in FIG. 2 or similar to FIG. 2 can be used for forming poly alpha olefins of the present disclosure.

As shown in FIG. 2, an apparatus 200 includes a feed line 102 coupled with a first reactor 104 (e.g., an oligomerization reactor). During use, a feed of feed line 102 can include an alpha olefin. First reactor 104 is coupled with filtration unit 202 via line 204. A gas chromatograph 134 is coupled with line 204. A sample may be removed from line 204 manually or using one or more valves (not shown) to direct, when in the open position, a portion of the first reactor effluent to gas chromatograph 134. A heat exchanger 206 is coupled with line 204 to provide heat to the first reactor effluent of line 204 and increase the tri-substituted vinylene dimer content of the first reactor effluent. The first reactor effluent (including intermediate PAO) of line 204 having increased tri-substituted vinylene dimer content is transferred to filtration unit 202 where particulates (if any) are filtered using a filter (e.g., a large-pore filter). Filtration unit 202 is coupled with a first distillation unit 106 via line 236. A filtration effluent (including intermediate PAO) of line 236 is transferred to first distillation unit 106 where byproducts and/or contaminants can be separated from the first reactor effluent. The first distillation unit 106 is coupled with a second distillation unit 110 via a line 130. A first distillation effluent (including intermediate PAO) flowing through the line 130 can be transferred to the second distillation unit 110. Second distillation unit 110 is coupled with a second reactor 116 (e.g., an oligomerization reactor) via line 118. A distillation effluent including dimers and unreacted monomers of line 118 is transferred to second reactor 116. A gas chromatograph 136 is coupled with line 118. A sample may be removed from line 118 manually or using one or more valves (not shown) to direct, when in the open position, a portion of the distillation effluent to gas chromatograph 136. Second distillation unit 110 is further coupled with a hydrogenation reactor 112 via line 114. A distillation effluent including trimers, tetramers, and higher oligomers (if any) of line 114 is transferred to the hydrogenation reactor 112. Second reactor 116 is coupled with the hydrogenation reactor 112 via line 132. An effluent of the second reactor (e.g., effluent including trimers) of line 132 is transferred to hydrogenation reactor 112. Alternatively, second reactor 116 can be coupled with a separate hydrogenation reactor (not shown) (e.g., not reactor 112). As shown in FIG. 1, hydrogenation reactor 112 is coupled with a third distillation unit 120 via line 122. A hydrogenated PAO product of line 122 is transferred to the third distillation unit 120 for separation into an ultra-low viscosity PAO (trimer) (removed by effluent line 126), a low to medium viscosity PAO (tetramer+) (removed by effluent line 128), and a lights fraction (dimer or lighter) (removed by effluent line 124).

Figure 3:
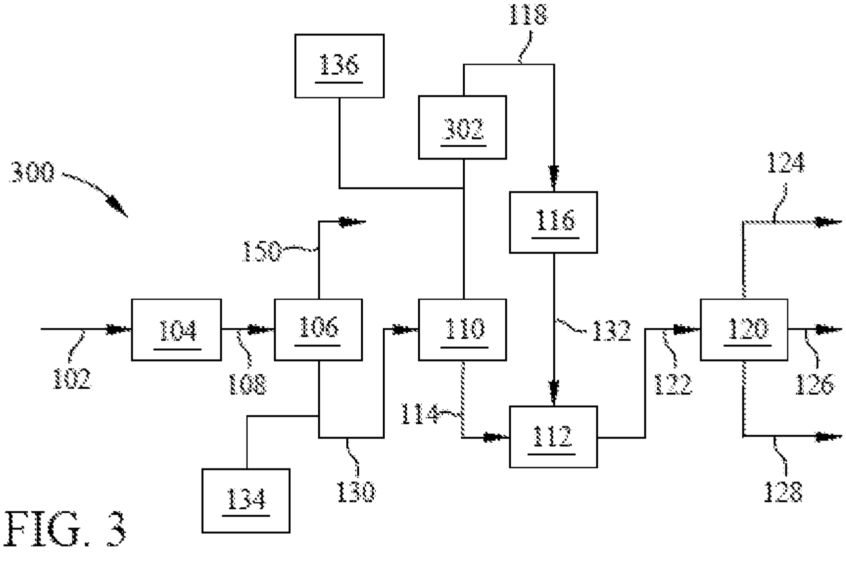
FIG. 3 is an apparatus for forming poly alpha olefins, according to at least one embodiment.

FIG. 3 is a diagram illustrating an apparatus for carrying out certain aspects of the present disclosure. More generally, a configuration shown in FIG. 3 or similar to FIG. 3 can be used for forming poly alpha olefins of the present disclosure.

As shown in FIG. 3, an apparatus 300 includes a feed line 102 coupled with a first reactor 104 (e.g., an oligomerization reactor). During use, a feed of feed line 102 can include an alpha olefin. First reactor 104 is coupled with a first distillation unit 106 via line 108. A first reactor effluent (including intermediate PAO) of line 108 is transferred to first distillation unit 106 where byproducts and/or contaminants can be separated from the first reactor effluent. First distillation unit 106 is coupled with a second distillation unit 110 via line 130. A first distillation effluent (including intermediate PAO) of line 130 is transferred to second distillation unit 110. A gas chromatograph 134 is coupled with line 130. A sample may be removed from line 130 manually or using one or more valves (not shown) to direct, when in the open position, a portion of the first distillation effluent to gas chromatograph 134. Second distillation unit 110 is coupled with a second reactor 116 (e.g., an oligomerization reactor) via line 118. A second distillation effluent including dimers and unreacted monomers of line 118 is transferred to second reactor 116. A gas chromatograph 136 is coupled with line 118. A sample may be removed from line 118 manually or using one or more valves (not shown) to direct, when in the open position, a portion of the second distillation effluent to gas chromatograph 136. A heat exchanger 302 is coupled with line 118 to provide heat to the distillation effluent and increase the tri-substituted vinylene dimer content of the distillation effluent that is then transferred to second reactor 116. A gas chromatograph (not shown) may be coupled with line 118 (between heat exchanger 302 and second reactor 116. A sample may be removed from line 118 (downstream of heat exchanger 302) manually or using one or more valves (not shown) to direct, when in the open position, a portion of the heated distillation effluent to the gas chromatograph. Second distillation unit 110 is further coupled with a hydrogenation reactor 112 via line 114. A distillation effluent including trimers, tetramers, and higher oligomers (if any) of line 114 is transferred to the hydrogenation reactor 112. Second reactor 116 is coupled with the hydrogenation reactor 112 via line 132. An effluent of the second reactor (e.g., effluent including trimers) of line 132 is transferred to hydrogenation reactor 112. Alternatively, second reactor 116 can be coupled with a separate hydrogenation reactor (not shown) (e.g., not reactor 112). As shown in FIG. 1, hydrogenation reactor 112 is coupled with a third distillation unit 120 via line 122. A hydrogenated PAO product of line 122 is transferred to the third distillation unit 120 for separation into an ultra-low viscosity PAO (trimer) (removed by effluent line 126), a low to medium viscosity PAO (tetramer+) (removed by effluent line 128), and a lights fraction (dimer or lighter) (removed by effluent line 124).

Embodiments Listing

The present disclosure provides, among others, the following embodiments, each of which may be considered as optionally including any alternate embodiments.

Clause 1. A process to produce a poly alpha olefin, the process comprising:

Introducing a first olefin monomer to a first catalyst and an activator in a first reactor to form a first reactor effluent comprising an olefin dimer and an olefin trimer;

introducing the first reactor effluent to a filtration unit to form a filtration effluent;

introducing the filtration effluent to a first distillation unit to form a first distillation effluent;

optionally introducing the first distillation effluent to a second distillation unit to form a second distillation effluent;

introducing the first distillation effluent and/or the second distillation effluent to a second catalyst in a second reactor to form a second reactor effluent comprising the olefin trimer;

removing a sample from (1) the first reactor, (2) a line coupling the first reactor to the filtration unit, (3) a line coupling the filtration unit to the first distillation unit or to the optional second distillation unit, (4) a line coupling the first distillation unit to the optional second distillation unit, or (5) a line coupling the first distillation unit or the optional second distillation unit to the second reactor; and introducing the sample to a gas chromatograph.

Clause 2. The process of Clause 1, wherein introducing the sample to the gas chromatograph comprises:

(1) introducing the sample to the gas chromatograph via a split/split-less injection port; and/or (2) providing to the gas chromatograph a first temperature of from about 30° C. to about 100° C.;

holding the first temperature for a time of from about 30 seconds to about 10 minutes;

increasing the first temperature to a second temperature at a rate from about 2° C. per minute to about 20° C. per minute and the second temperature is from about 60° C. to about 250° C.;

holding the second temperature for a time from about 30 seconds to about 20 minutes;

increasing the second temperature to a third temperature at a rate from about 10° C. per minute to about 40° C. per minute, and the third temperature is from about 200° C. to about 350° C.; and holding the third temperature for a time from about 30 seconds to about 30 minutes.

Clause 3. The process of Clause 1 or Clause 2, wherein:

the first temperature is about 60° C., and the first temperature is held for about 1 minute;

the first temperature is increased to the second temperature at a rate of about 10° C. per minute and the second temperature is about 180° C.;

the second temperature is held for a time of about 5 minutes;

the second temperature is increased to the third temperature at a rate of about 25° C. per minute, and the third temperature is about 250° C.; or the third temperature is held for a time of about 8 minutes.

Clause 4. The process of any of Clauses 1 to 3, wherein:

the first temperature is about 60° C., and the first temperature is held for about 1 minute;

the first temperature is increased to the second temperature at a rate of about 10° C. per minute and the second temperature is about 180° C.;

the second temperature is held for a time of about 5 minutes;

the second temperature is increased to the third temperature at a rate of about 25° C. per minute, and the third temperature is about 250° C.; and the third temperature is held for a time of about 8 minutes.

Clause 5. The process of any of Clauses 1 to 4, further comprising heating the first reactor effluent to form an isomerized product.

Clause 6. The process of any of Clauses 1 to 5, further comprising introducing the second reactor effluent to a third reactor and hydrogenating the second reactor effluent to form a hydrogenated effluent.

Clause 7. The process of any of Clauses 1 to 6, further comprising transferring the hydrogenated effluent to a third distillation unit to form an ultra-low viscosity poly alpha olefin effluent.

Clause 8. The process of any of Clauses 1 to 7, wherein the first catalyst is a metallocene catalyst and the second catalyst comprises $BF_3$.

Clause 9. The process of any of Clauses 1 to 8, wherein heating comprises providing heat to a line via one or more heat exchangers, the line comprising the first reactor effluent.

Clause 10. The process of any of Clauses 1 to 9, wherein the isomerized product comprises greater than 85 wt % of tri-substituted vinylene dimer.

Clause 11. The process of any of Clauses 1 to 10, wherein the isomerized product comprises greater than 95 wt % of tri-substituted vinylene dimer.

Clause 12. The process of any of Clauses 1 to 11, wherein heating is performed at a temperature of about 270° C. or greater.

Clause 13. The process of any of Clauses 1 to 12, wherein heating is performed at a pressure of about 100 psi to about 600 psi.

Clause 14. The process of any of Clauses 1 to 13, wherein introducing the isomerized product to the filtration unit comprises introducing the isomerized product to a particulate filter having an average pore size of from about 5 microns to about 20 microns.

Clause 15. The process of any of Clauses 1 to 14, wherein introducing the isomerized product to the filtration unit comprises flowing the isomerized product through the filtration unit at a rate of from about 10 lbs/min to about 300 lbs/min.

Clause 16. A process to produce a poly alpha olefin, the process comprising:

introducing a first olefin monomer to a first catalyst and an activator in a first reactor to form a first reactor effluent comprising an olefin dimer and an olefin trimer;

introducing the first reactor effluent to a first distillation unit to form a first distillation effluent;

optionally introducing the first distillation effluent to a second distillation unit to form a second distillation effluent;

introducing the first reactor effluent and/or the second distillation effluent to a second catalyst in a second reactor to form a second reactor effluent comprising the olefin trimer;

removing a sample from (1) the first reactor, (2) a line coupling the first reactor to the first distillation unit; (3) a line coupling the first distillation unit to the second distillation unit, or (4) a line coupling the distillation unit to the second reactor; and introducing the sample to a gas chromatograph having a column coated with a material (such as a non-polar material or wherein the material is selected from the group consisting of heavy-wax, diphenyl, dimethyl polysiloxane, polyethylene glycol, or fused silica).

Clause 17. The process of Clause 16, wherein introducing the sample to the gas chromatograph comprises:
- providing to the gas chromatograph a first temperature of from about 30° C. to about 100° C.;
- holding the first temperature for a time of from about 30 seconds to about 10 minutes;
- increasing the first temperature to a second temperature at a rate from about 2° C. per minute to about 20° C. per minute and the second temperature is from about 60° C. to about 250° C.;
- holding the second temperature for a time from about 30 seconds to about 20 minutes;
- increasing the second temperature to a third temperature at a rate from about 10° C. per minute to about 40° C. per minute, and the third temperature is from about 200° C. to about 350° C.; and
- holding the third temperature for a time from about 30 seconds to about 30 minutes.

Clause 18. The process of Clause 16 or 17, wherein:
- the first temperature is about 60° C., and the first temperature is held for about 1 minute;
- the first temperature is increased to the second temperature at a rate of about 10° C. per minute and the second temperature is about 180° C.;
- the second temperature is held for a time of about 5 minutes;
- the second temperature is increased to the third temperature at a rate of about 25° C. per minute, and the third temperature is about 250° C.; or the third temperature is held for a time of about 8 minutes.

Clause 19. The process of any of Clauses 16 to 18, wherein:
- the first temperature is about 60° C., and the first temperature is held for about 1 minute;
- the first temperature is increased to the second temperature at a rate of about 10° C. per minute and the second temperature is about 180° C.;
- the second temperature is held for a time of about 5 minutes;
- the second temperature is increased to the third temperature at a rate of about 25° C. per minute, and the third temperature is about 250° C.; and
- the third temperature is held for a time of about 8 minutes.

Clause 20. The process of any of Clauses 16 to 19, further comprising heating the second distillation effluent to form an isomerized product.

Clause 21. The process of any of Clauses 16 to 20, further comprising introducing the second reactor effluent to a third reactor and hydrogenating the second reactor effluent to form a hydrogenated effluent.

Clause 22. The process of any of Clauses 16 to 21, further comprising transferring the hydrogenated effluent to a third distillation unit to form an ultra-low viscosity poly alpha olefin effluent.

Clause 23. The process of any of Clauses 16 to 22, wherein the first catalyst is a metallocene catalyst and the second catalyst is a Lewis acid (such as $BF_3$).

Clause 24. The process of any of Clauses 16 to 23, wherein heating comprises providing heat to a line comprising the first distillation effluent via one or more heat exchangers.

Clause 25. The process of any of Clauses 16 to 24, wherein the isomerized product comprises greater than 85 wt % of tri-substituted vinylene dimer.

Clause 26. The process of any of Clauses 16 to 25, wherein the isomerized product comprises greater than 95 wt % of tri-substituted vinylene dimer.

Clause 27. The process of any of Clauses 16 to 26, wherein heating is performed at a temperature of about 270° C. or greater.

Clause 28. The process of any of Clauses 16 to 27, wherein heating is performed at a pressure of about 100 psi to about 600 psi.

Clause 29. A process to produce a poly alpha olefin, the process comprising:
- introducing a first olefin monomer to a first catalyst and an activator in a first reactor to form a first reactor effluent comprising an olefin dimer and an olefin trimer;
- introducing the first reactor effluent to a first distillation unit to form a first distillation effluent;
- introducing the first distillation effluent to a second distillation unit to form a second distillation effluent;
- introducing the second distillation effluent to a second catalyst in a second reactor to form a second reactor effluent comprising the olefin trimer;
- removing a sample from (1) the first reactor, (2) a line coupling the first reactor to the first distillation unit; (3) a line coupling the first distillation unit to the second distillation unit, or (4) a line coupling the distillation unit to the second reactor; and introducing the sample to a gas chromatograph.

Clause 30. The process of Clause 29, introducing the sample to the gas chromatograph comprises:
- providing to the gas chromatograph a first temperature of from about 30° C. to about 100° C.;
- holding the first temperature for a time of from about 30 seconds to about 10 minutes;
- increasing the first temperature to a second temperature at a rate from about 2° C. per minute to about 20° C. per minute and the second temperature is from about 60° C. to about 250° C.;
- holding the second temperature for a time from about 30 seconds to about 20 minutes;
- increasing the second temperature to a third temperature at a rate from about 10° C. per minute to about 40° C. per minute, and the third temperature is from about 200° C. to about 350° C.; and
- holding the third temperature for a time from about 30 seconds to about 30 minutes.

Clause 31. The process of Clause 29 or 30, wherein:
- the first temperature is about 60° C., and the first temperature is held for about 1 minute;
- the first temperature is increased to the second temperature at a rate of about 10° C. per minute and the second temperature is about 180° C.;
- the second temperature is held for a time of about 5 minutes;
- the second temperature is increased to the third temperature at a rate of about 25° C. per minute, and the third temperature is about 250° C.; or
- the third temperature is held for a time of about 8 minutes.

Clause 32. The process of any of Clauses 29 to 31, wherein:
- the first temperature is about 60° C., and the first temperature is held for about 1 minute;
- the first temperature is increased to the second temperature at a rate of about 10° C. per minute and the second temperature is about 180° C.;
- the second temperature is held for a time of about 5 minutes;

the second temperature is increased to the third temperature at a rate of about 25° C. per minute, and the third temperature is about 250° C.; and the third temperature is held for a time of about 8 minutes.

Clause 33. The process of any of Clauses 29 to 32, further comprising introducing the second reactor effluent to a third reactor and hydrogenating the second reactor effluent to form a hydrogenated effluent.

Clause 34. The process of any of Clauses 29 to 33, further comprising transferring the hydrogenated effluent to a third distillation unit to form an ultra-low viscosity poly alpha olefin effluent.

Clause 35. The process of any of Clauses 29 to 34, wherein the first catalyst is a metallocene catalyst and the second catalyst is a Lewis acid.

Clause 36. An apparatus comprising:

a first reactor coupled at a first end with a first end of a first distillation unit via a first line;

a gas chromatograph coupled at a first end with the first line; and a second distillation unit coupled with:

a second end of the first distillation unit at a first end of the second distillation unit, a first end of a second reactor at a second end of the second distillation unit via a second line, and a first end of a hydrogenation unit at a third end of the second distillation unit.

Clause 37. The apparatus of Clause 36, further comprising a second gas chromatograph coupled with the second line.

Clause 38. The apparatus of Clause 36 or 37, further comprising a heat exchanger coupled with the first line and/or second line.

Clause 39. The apparatus of any of Clauses 36 to 38, further comprising a third distillation unit coupled at a first end with a second end of the hydrogenation unit.

Clause 40. The apparatus of any of Clauses 36 to 39, wherein the second reactor is coupled with the hydrogenation unit.

Clause 41. An apparatus comprising:

a first reactor coupled at a first end with a first end of a filtration unit;

a first distillation unit coupled at a first end with a second end of the filtration unit;

a second distillation unit coupled with:

a second end of the first distillation unit, via a first line, at a first end of the second distillation unit, a first end of a second reactor, via a second line, at a second end of the second distillation unit, and a first end of a hydrogenation unit at a third end of the second distillation unit; and a gas chromatograph coupled at a first end with the second line.

Clause 42. The apparatus of Clause 41, further comprising a gas chromatograph coupled with the first line.

Clause 43. The apparatus of Clause 41 or 42, further comprising a heat exchanger coupled with the second line.

Clause 44. The apparatus of any of Clauses 41 to 43, further comprising a third distillation unit coupled at a first end with a second end of the hydrogenation unit.

Clause 45. The apparatus of any of Clauses 41 to 44, wherein the second reactor is coupled with the hydrogenation unit.

Clause 46. A process to produce a poly alpha olefin, the process comprising:

introducing a first olefin monomer to a first catalyst and an activator in a first reactor to form a first reactor effluent comprising an olefin dimer and an olefin trimer;

introducing the first reactor effluent to a filtration unit to form a filtration effluent;

introducing the filtration effluent to a distillation unit to form a distillation effluent;

removing a sample from (1) the first reactor, (2) a line coupling the first reactor to the filtration unit, or (3) a line coupling the filtration unit to the distillation unit; and introducing the sample to a gas chromatograph.

Clause 47. The process of Clause 46, further comprising:

introducing the first distillation effluent and/or a second distillation effluent to a second catalyst in a second reactor to form a second reactor effluent comprising the olefin trimer;

optionally removing a second sample from (4) a line coupling the distillation unit to a second reactor, or (5) a line coupling the first distillation unit to an optional second distillation unit; and introducing the first sample or the second sample to the gas chromatograph or a second gas chromatograph.

Clause 48. The process of Clauses 46, wherein introducing the first sample or the second sample to the gas chromatograph or the second gas chromatograph comprises:

(1) introducing the first sample or the second sample to the gas chromatograph via a split/split-less injection port; and/or (2) providing to the gas chromatograph a first temperature of from about 30° C. to about 100° C.;

holding the first temperature for a time of from about 30 seconds to about 10 minutes;

increasing the first temperature to a second temperature at a rate from about 2° C. per minute to about 20° C. per minute and the second temperature is from about 60° C. to about 250° C.;

holding the second temperature for a time from about 30 seconds to about 20 minutes;

increasing the second temperature to a third temperature at a rate from about 10° C. per minute to about 40° C. per minute, and the third temperature is from about 200° C. to about 350° C.; and holding the third temperature for a time from about 30 seconds to about 30 minutes.

Clause 49. The process of any of Clauses 46 to Clause 48, wherein:

the first temperature is about 60° C., and the first temperature is held for about 1 minute;

the first temperature is increased to the second temperature at a rate of about 10° C. per minute and the second temperature is about 180° C.;

the second temperature is held for a time of about 5 minutes;

the second temperature is increased to the third temperature at a rate of about 25° C. per minute, and the third temperature is about 250° C.; or the third temperature is held for a time of about 8 minutes.

Clause 50. The process of any of Clauses 46 to 49, wherein:

the first temperature is about 60° C., and the first temperature is held for about 1 minute;

the first temperature is increased to the second temperature at a rate of about 10° C. per minute and the second temperature is about 180° C.;

the second temperature is held for a time of about 5 minutes;

the second temperature is increased to the third temperature at a rate of about 25° C. per minute, and the third temperature is about 250° C.; and the third temperature is held for a time of about 8 minutes.

Clause 51. The process of any of Clauses 46 to 50, further comprising heating the first reactor effluent to form an isomerized product.

Clause 52. The process of any of Clauses 46 to 51, further comprising introducing the second reactor effluent to a third reactor and hydrogenating the second reactor effluent to form a hydrogenated effluent.

Clause 53. The apparatus of any of Clauses 46 to 51, further comprising a gas chromatograph coupled with a third line coupled with the third reactor.

Clause 54. A process for measuring olefin content in a feed comprising olefins, comprising:
- introducing a sample to a gas chromatograph, the sample comprising dimers and/or trimers of linear alpha olefins, wherein introducing the sample to the gas chromatograph comprises:
  - providing to the gas chromatograph a first temperature of from about 30° C. to about 100° C.;
  - holding the first temperature for a time of from about 30 seconds to about 10 minutes;
  - increasing the first temperature to a second temperature at a rate from about 2° C. per minute to about 20° C. per minute and the second temperature is from about 60° C. to about 250° C.;
  - holding the second temperature for a time from about 30 seconds to about 20 minutes;
  - increasing the second temperature to a third temperature at a rate from about 10° C. per minute to about 40° C. per minute, and the third temperature is from about 200° C. to about 350° C.; and
  - holding the third temperature for a time from about 30 seconds to about 30 minutes.

Clause 55. The process of Clause 54, further comprising increasing the third temperature to a fourth temperature at a rate from about 10° C. per minute to about 40° C. per minute, and the fourth temperature is from about 380° C. to about 400° C.

Clause 56. The process of Clauses 54 or 55, further comprising holding the fourth temperature for a time from about 30 seconds to about 10 minutes.

Clause 57. The process of any of Clauses 54 to 56, wherein:
- the first temperature is about 60° C., and the first temperature is held for about 1 minute;
- the first temperature is increased to the second temperature at a rate of about 10° C. per minute and the second temperature is about 180° C.;
- the second temperature is held for a time of about 5 minutes;
- the second temperature is increased to the third temperature at a rate of about 25° C. per minute, and the third temperature is about 250° C.; or
- the third temperature is held for a time of about 8 minutes.

Clause 58. The process of any of Clauses 54 to 57, wherein:
- the first temperature is about 60° C., and the first temperature is held for about 1 minute;
- the first temperature is increased to the second temperature at a rate of about 10° C. per minute and the second temperature is about 180° C.;
- the second temperature is held for a time of about 5 minutes;
- the second temperature is increased to the third temperature at a rate of about 25° C. per minute, and the third temperature is about 250° C.; and
- the third temperature is held for a time of about 8 minutes.

Clause 59. The process of any of Clauses 54 to 58, wherein the sample comprises $C_6$-$C_{20}$ dimers.

Clause 60. The process of any of Clauses 54 to 59, further comprising:
- calculating a ratio of cis-dimers to trans-dimers or a ratio of trans-dimers to cis-dimers based on information obtained from a gas chromatogram obtained from the gas chromatograph.

Clause 61. The process of any of Clauses 54 to 60, wherein the sample comprises greater than 45 wt % of tri-substituted vinylene dimer.

EXAMPLES

Experimental

Example 1: High Vinylidene Dimer

Dimer was generated from dimerization of 1-decene using dimethylsilylbis(4,5,6,7-tetrahydroindenyl) zirconium dimethyl,N,N-dimethylanilinium tetrakis (pentafluorophenyl) borate and tri n-octyl aluminum (TNOA) as the catalyst/activator system. The sample was then distilled without addition of body feed or filtration to generate >98% dimer. An initial NMR was taken to confirm the distribution of vinylidene to trisubstituted olefin. The dimer was then heated to the following temperatures under nitrogen while stirring for 10 hours. Multiple samples were removed during the reaction at given time points, as shown in the chart below.

TABLE 1

Sampling Schedule for Example 1

| Sample # | Total Time (h) | Temperature (° C.) |
|---|---|---|
| 0 | 0 | 25 |
| 1 | 1 | 200 |
| 2 | 2 | 250 |
| 3 | 3 | 270 |
| 4 | 7 | 270 |
| 5 | 8 | 295 |
| 6 | 10 | 295 |

Figure 6:
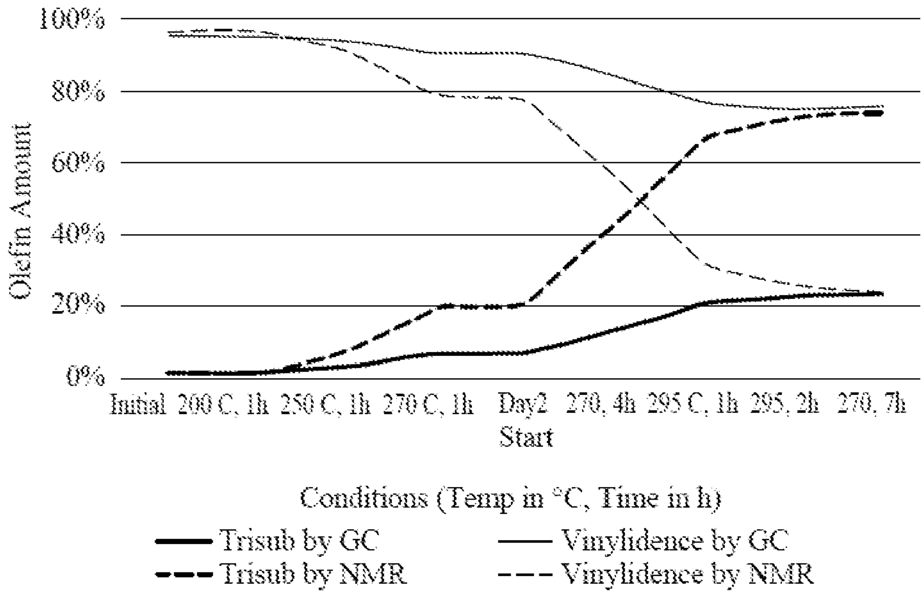
FIG. 6 is a graph illustrating normalized amount of vinylidene and trisubstituted olefin at given temperature and time points for dimer samples, according to at least one embodiment.
Figure 7A:
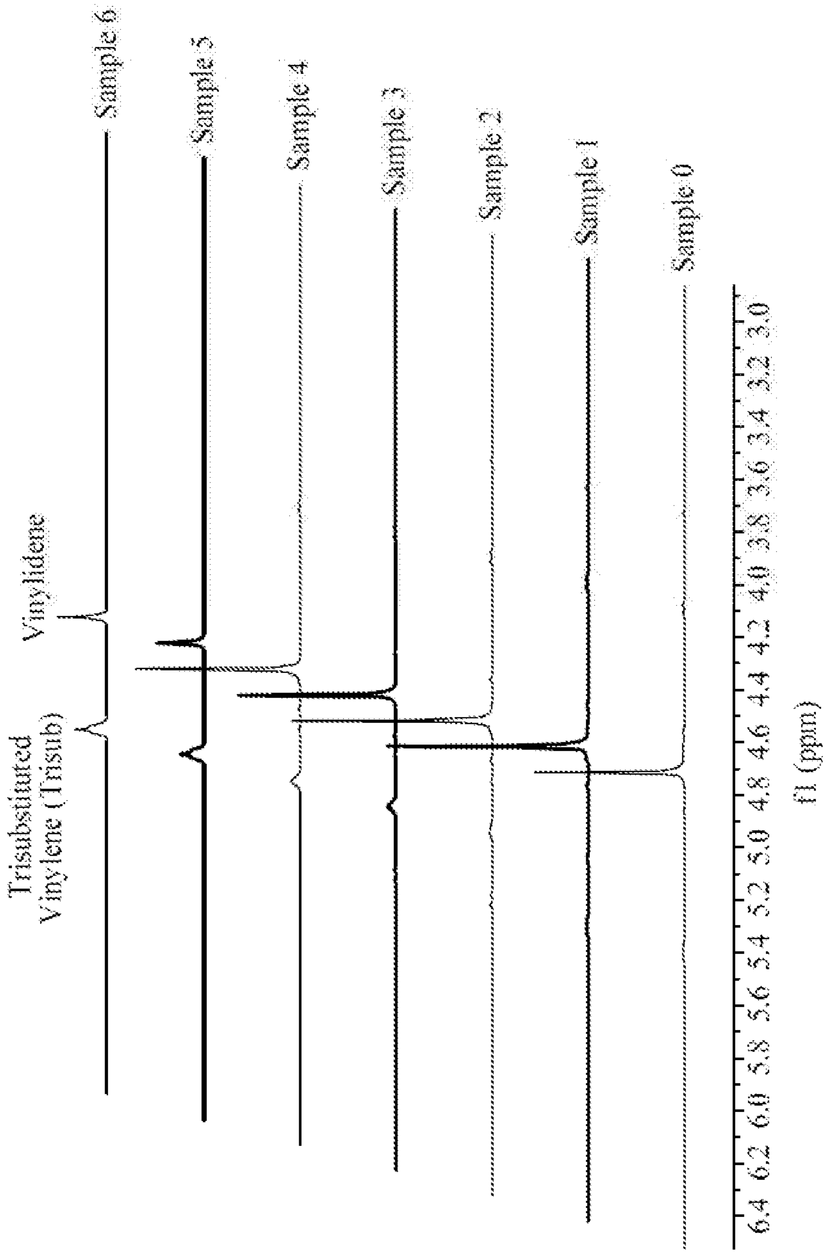
FIG. 7A is nuclear magnetic spectra of dimer samples, according to at least one embodiment.
Figure 7B:
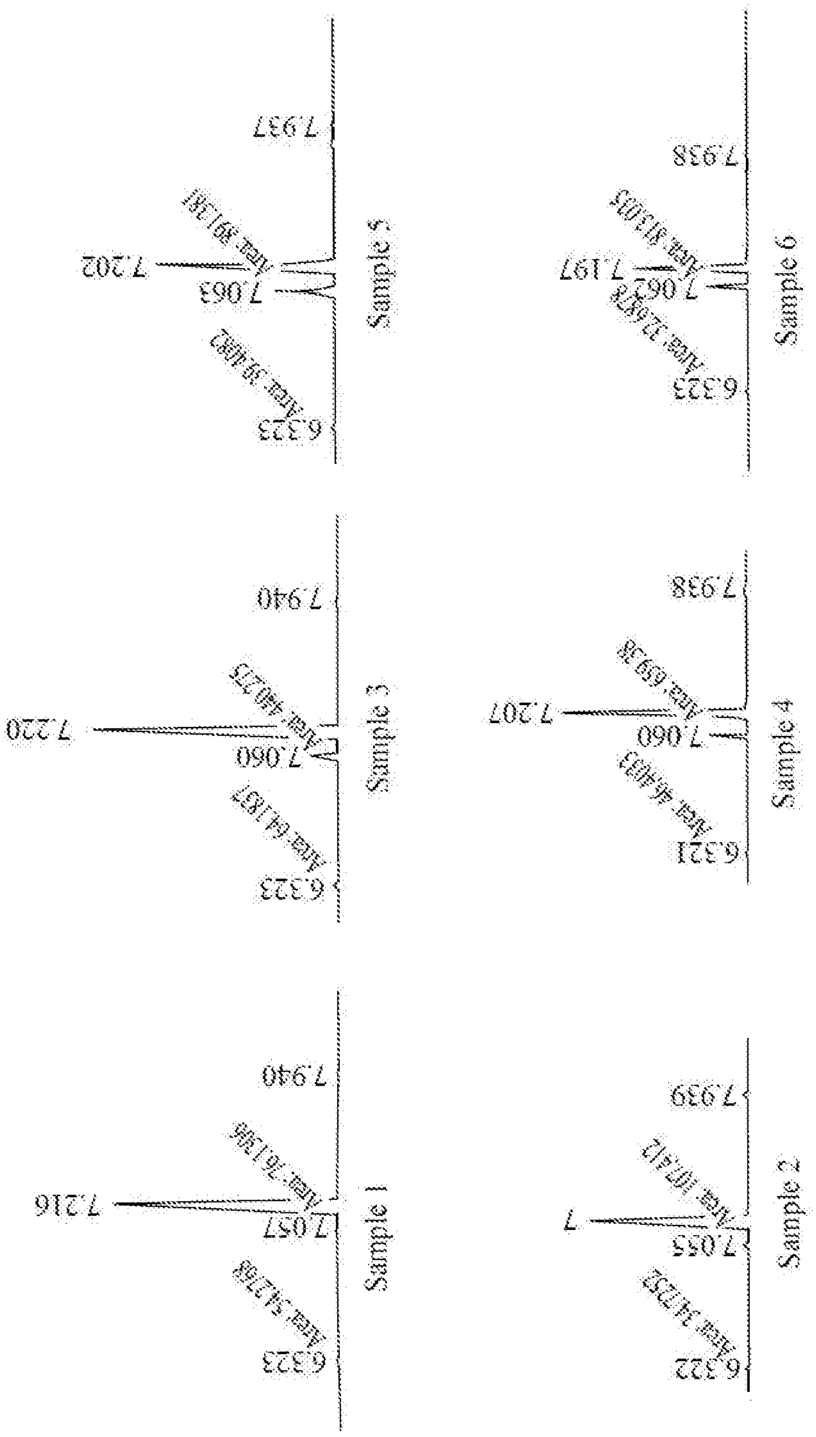
FIG. 7B is gas chromatographs of dimer samples, according to at least one embodiment.

During the reaction all samples were analyzed by both NMR and GC. The spectra by NMR and GC are shown FIGS. 7A and 7B, respectively. The NMR region between 4.5-6.5 ppm represents the olefinic protons. A peak at ~5.1 ppm represents the trisubstituted vinyl olefins and the peak at 4.7 represents the vinylidene olefins. The GC spectra of samples 1-6 of the same experiment are shown in FIG. 7B, showing a vinylidene peak at 7.22 min and trisubstituted vinyl olefins at 7.06. The graphs plotting the ratio between trisubstituted vinyl olefin and vinylidene olefin using GC and NMR are shown versus time in FIG. 6, which illustrates the discrepancy between analogous samples from a representative isomerization run. Initially, both GC and NMR had predominantly vinylidene dimer. As the reaction proceeded, the amount of trisubstituted vinylene increased in both NMR and GC. By the end of the reaction, the GC data varied significantly in both the vinylidene and trisubstituted olefin distribution. The initial ratio of trisubstituted olefin to vinylidene olefin is approximately 1:96 but significant isomerization of the olefin to the trisubstituted olefin occurs during 10 hours of heating to give a ratio of 1:2.8 by GC but 1:0.36 by NMR. Despite clean spectra, the GC data did not correlate well to NMR. It was hypothesized that a second trisubstituted olefin peak overlapped with the vinylidene peak.

Figure 8:
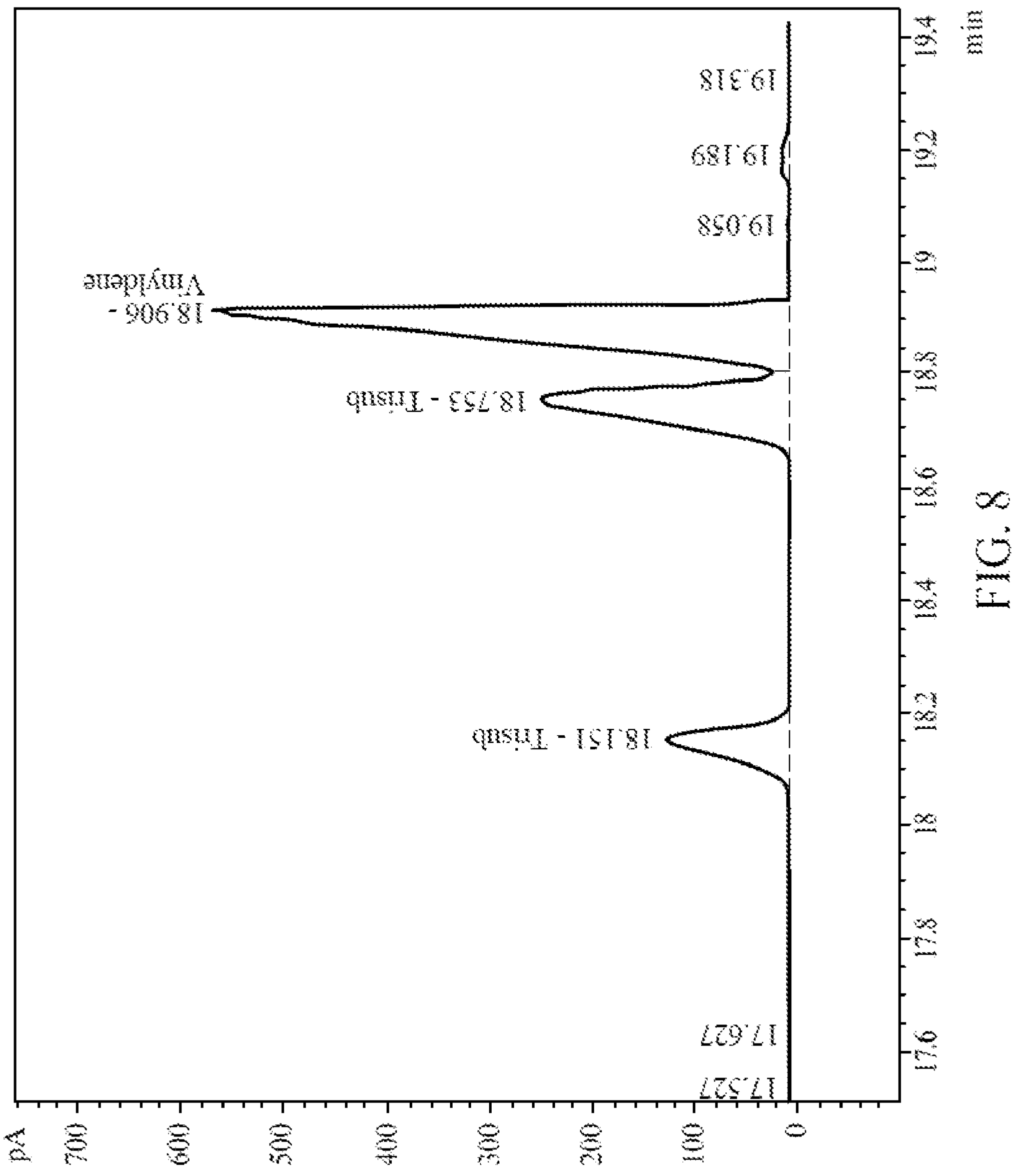
FIG. 8 is a gas chromatograph of a dimer sample, according to at least one embodiment.

Upon modification of the GC process, a third peak was able to be fully resolved by GC, as shown in FIG. 8. The total of the two trisubstituted peaks correlated well with the corresponding NMR data. By GCMS, these two isomers had identical mass, thus it was hypothesized that these are the cis-trisubstituted vinylene and trans-trisubstituted vinylene isomers.

Figure 4:
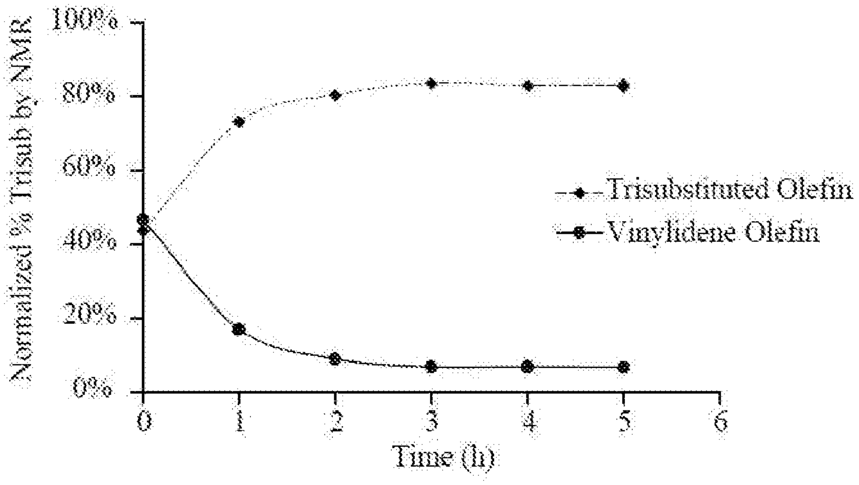
FIG. 4 is a graph illustrating normalized % tri-substituted vinylene dimers versus time, according to at least one embodiment.
Figure 9:
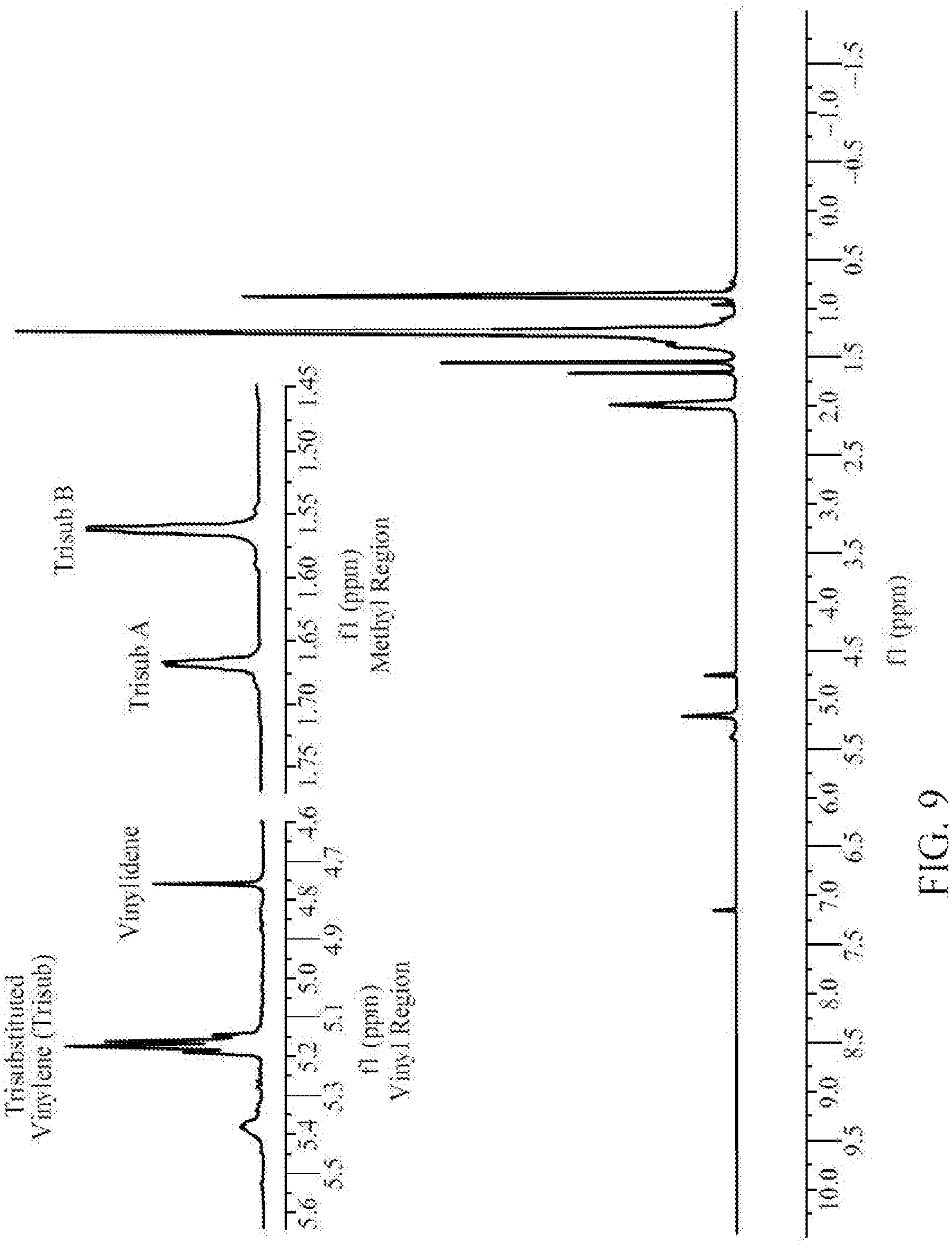
FIG. 9 is an NMR spectrum illustrating trisubstituted olefins, according to at least one embodiment.

Example 2: Dimer sample was generated from dimerization of 1-decene using dimethylsilylbis(4,5,6,7-tetrahydroindenyl) zirconium dimethyl, N,N-dimethylanilinium tetrakis (pentafluorophenyl) borate and tri n-octyl aluminum (TNOA) as the catalyst/activator system. The sample was then distilled without addition of body feed or filtration to generate >98% dimer. An initial NMR was taken to confirm the distribution of vinylidene to trisubstituted olefin, shown in FIG. 7A. The two trisubstituted vinylene isomers are highlighted in the $^1$H NMR, showing overlap in the olefinic protons at ~5.1 ppm but two distinct methyl peaks at ~1.67 and 1.56 ppm. These peaks correlate to the two trisubstituted vinylene isomers observed by GC. The sample was then heated to 270° C. under nitrogen while stirring for over 22 hours and multiple samples were removed from the pot. All samples were analyzed by NMR and GC, and the resulting ratios of trisubstituted olefin to vinylidene olefin are reported in FIG. 4. The initial ratio of trisubstituted olefin to vinylidene olefin is approximately 1:1 but significant isomerization of the olefin to the trisubstituted olefin occurs within 2 hours to give a ratio of 9:1. FIG. 9 is an NMR spectrum illustrating trisubstituted olefins, according to at least one embodiment.

Figure 5:
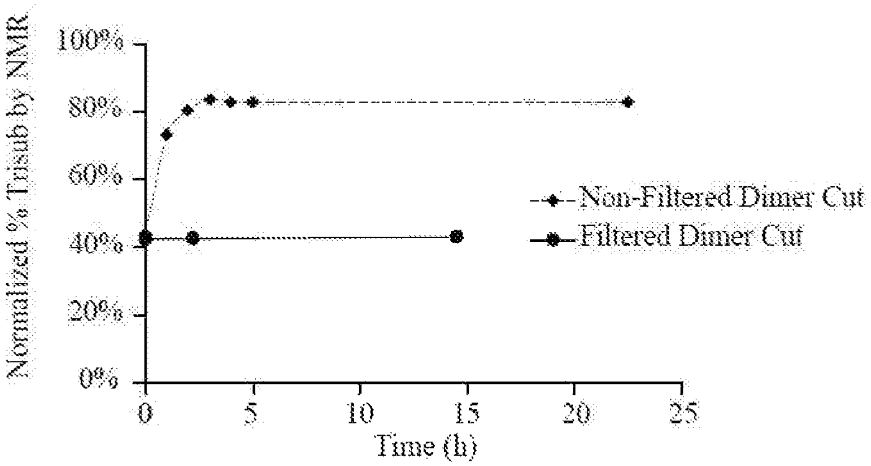
FIG. 5 is a graph illustrating normalized % tri-substituted vinylene dimers versus time, according to at least one embodiment.

Comparative Example 1: Dimer sample generated from an analogous process as sample 2 was mixed with cellulosic body feed and the slurry was filtered to remove all polar components. The sample was then distilled to generate >98% dimer. An initial NMR was taken to confirm the distribution of vinylidene to trisubstituted olefin. The sample was then heated to 270° C. under nitrogen while stirring for over 14 hours and multiple samples were removed from the pot. Samples were analyzed by NMR. The comparison of trisubstituted dimer over analogous reaction times is shown in FIG. 5. This example illustrates that the dimer sample generated from bypassing filtration results in significant isomerization to generate higher trisubstituted olefin. FIG. 5 further indicates that a dimer sample that has undergone filtration prior to isomerization exhibits no change in the amount of trisubstituted olefin.

Comparative Example 2: The dimer sample from comparative example 1 was combined with 0.7 wt % Amberlyst 15 catalyst, and heated under nitrogen while stirring to 100° C. for over 22 hours. An initial NMR confirmed the distribution of vinylidene to trisubstituted vinylene olefin as ~1:1. After 22 hours, the ratio was 1:29 vinylidene to trisubstituted vinylene olefin by NMR.

Materials and Processes for the Above Examples

Samples were analyzed by $^1$H NMR using a 500 Hz Bruker, diluted in $CD_3Cl$ or $C_6D_6$. Samples were also generated by GC using an Agilent GC, using the process below:

TABLE 2

| Example GC Process | |
| --- | --- |
| Inlet Temperature | 280° C. |
| Detector Temperature | 280° C. |
| Sample Temp. Program | Initial 60° C. hold for 1 min |
| | Ramp @10° C./min to 180° C., hold for 5 min |
| | Ramp @25° C./min to 250° C., hold for 8 min |

TABLE 2-continued

| Example GC Process | |
| --- | --- |
| Column Flow | 2 mL/min |
| Split | Split mode; 125:1 |
| Injector | Autosampler (0.1 μL) |
| Column Parameters | DBWaxetr 122-7362 Capillary Column; 60 m × 0.25 mm × 0.25 μm |

Overall, the present disclosure provides processes and apparatuses for forming poly alpha olefins. Processes can include measuring by gas chromatography an amount of one or more of vinylidene dimers and/or trisubstituted dimers (such as cis-trisubstituted dimers and trans-trisubstituted dimers). Processes include optionally isomerizing the vinylidene dimers to form tri-substituted olefin dimers (such as cis-trisubstituted dimers and trans-trisubstituted dimers). Measuring by gas chromatography an amount of one or more of vinylidene dimers and/or trisubstituted dimers (such as cis-trisubstituted dimers and/or trans-trisubstituted dimers) can provide monitoring of dimer formation in commercial scale poly alpha olefin production, such as production of low viscosity poly alpha olefins.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the present disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While the present disclosure has been described with respect to a number of embodiments and examples, those skilled in the art, having benefit of this disclosure, will appreciate that other embodiments can be devised which do not depart from the scope and spirit of the present disclosure.

What is claimed is:

1. A process to produce a poly alpha olefin, the process comprising:

introducing a first olefin monomer to a first catalyst and an activator in a first reactor to form a first reactor effluent comprising olefin dimers;

introducing the first reactor effluent to a distillation unit to form a distillation effluent comprising olefin dimers;

introducing the distillation effluent to a second catalyst and a second olefin monomer in a second reactor to form a second reactor effluent comprising the poly alpha olefin, wherein the poly alpha olefin comprises olefin trimers;

removing a first sample from a first line extending between the first reactor and the distillation unit and removing a second sample from a second line extending between the distillation unit and the second reactor;

measuring an amount of the olefin dimers in each of the first and second samples in one or more gas chromatographs in substantially real-time, wherein the olefin dimers comprise vinylidene dimers and/or trisubstituted dimers, wherein the trisubstituted dimers comprise cis-trisubstituted dimers and/or trans-trisubstituted dimers; and adjusting one or more process conditions to increase an amount of the trisubstituted dimers, wherein adjusting the one or more process conditions comprises adjusting one or more reactor conditions for the first reactor, adjusting one or more distillation conditions of the distillation unit, heating the first reactor effluent flowing through the first line, and/or heating the distillation effluent flowing through the second line.

2. The process of claim 1, further comprising: isomerizing the vinylidene dimers in the first reactor effluent, the distillation effluent, or both to form an isomerized product, wherein the isomerized product comprises trisubstituted dimers.

3. The process of claim 2, wherein the isomerizing comprises heating the first reactor effluent, the distillation effluent, or both.

4. The process of claim 3, wherein the heating comprises heating the first reactor effluent flowing through the first line with one or more first heat exchangers, heating the distillation effluent flowing through the second line with one or more second heat exchangers, or both.

5. The process of claim 3, wherein the first reactor effluent, the distillation effluent, or both is heated to a temperature of about 200° C. or greater.

6. The process of claim 3, wherein the isomerizing occurs in absence of an isomerization catalyst.

7. The process of claim 3, wherein the isomerizing occurs in absence of an isomerization reactor.

8. The process of claim 6, wherein the first catalyst is a metallocene catalyst and the second catalyst is Lewis acid.

9. The process of claim 2, further comprising:

introducing the isomerized product to a filtration unit to form a filtration effluent which is introduced to a first distillation unit, wherein the filtration unit has an average pore size of from about 5 to about 20 microns.

10. The process of claim 2, wherein the isomerized product comprises a molar ratio of cis-trisubstituted dimers to trans-trisubstituted dimers ranging from about 10:1 to about 1:10.

11. The process of claim 2, wherein the isomerized product comprises less than 70 wt.% of di-substituted Vinylidene dimers.

12. The process of claim 1, wherein the measuring in the one or more gas chromatographs comprises:

setting the one or more gas chromatographs to a first temperature from about 30° C. to about 100° C.;

holding the first temperature for a time from about 30 seconds to about 10 minutes;

increasing the first temperature to a second temperature at a rate from about 1° C. per minute to about 20° C. per minute and the second temperature is from about 60° C. to about 250° C.;

holding the second temperature for a time from about 30 seconds to about 20 minutes;

increasing the second temperature to a third temperature at a rate from about 2° C. per minute to about 40° C. per minute, and the third temperature is from about 200° C. to about 350° C.; and holding the third temperature for a time from about 30 seconds to about 30 minutes.

13. The process of claim 3; wherein:

the first temperature is about 60° C.; and the first temperature is held for about 1 minute;

the first temperature is increased to the second temperature at a rate of about 10° C. per minute and the second temperature is about 180° C.;

the second temperature is held for a time of about 5 minutes;

the second temperature is increased to the third temperature at a rate of about 25° C. per minute; and the third temperature is about 250° C.; or the third temperature is held for a time of about 8 minutes.

14. The process of claim 1, wherein the one or more gas chromatographs comprises a column coated with a material comprising heavy wax, diphenyl, dimethyl polysiloxane, polyethylene glycol, or fused silica.

15. The process of claim 1, wherein the first and/or second sample comprises $C_6$-$C_{20}$ dimers.

16. The process of claim 1, wherein the first and/or second sample comprises greater than 45 wt. % of trisubstituted dimer.

17. The process of claim 16, wherein the first and/or second sample comprises greater than 85 wt. % of trisubstituted dimer.

18. The process of claim 1, wherein the second olefin monomer is the same as the first olefin monomer.

19. The process of claim 1, wherein the poly alpha olefin further comprises dimers.

20. The process of claim 1, wherein adiusting the one or more process conditions comprises adiusting the one or more reactor conditions, and wherein the one or more reactor conditions comprise a reaction temperature.

21. The process of claim 1, wherein the first sample is measured in a first gas chromatograph and the second sample is measured in a second gas chromatograph.

* * * * *